US012564492B2

(12) United States Patent
Badhwar et al.

(10) Patent No.: US 12,564,492 B2
(45) Date of Patent: Mar. 3, 2026

(54) RETRIEVABLE SELF-EXPANDING NON-THROMBOGENIC LOW-PROFILE PERCUTANEOUS ATRIOVENTRICULAR VALVE PROSTHESIS

(71) Applicant: University of Pittsburgh—Of the Commonwealth System of Higher Education, Pittsburgh, PA (US)

(72) Inventors: Vinay Badhwar, Washington, PA (US); Young Jae Chun, Wexford, PA (US); Antonio D'Amore, Pittsburgh, PA (US); David S. Schwartzman, Pittsburgh, PA (US); William R. Wagner, Gibsonia, PA (US)

(73) Assignees: University of Pittsburgh—Of the Commonwealth System of Higher Education, Pittsburgh, PA (US); Ri.MED Foundation, Palermo (IT)

( * ) Notice: Subject to any disclaimer, the term of this patent is extended or adjusted under 35 U.S.C. 154(b) by 97 days.

(21) Appl. No.: 18/446,789

(22) Filed: Aug. 9, 2023

(65) Prior Publication Data

US 2024/0108461 A1 Apr. 4, 2024

Related U.S. Application Data

(63) Continuation of application No. 16/777,007, filed on Jan. 30, 2020, now Pat. No. 11,771,555, which is a
(Continued)

(51) Int. Cl.
*A61F 2/24* (2006.01)
*A61L 27/14* (2006.01)
(Continued)

(52) U.S. Cl.
CPC .......... *A61F 2/2418* (2013.01); *A61F 2/2409* (2013.01); *A61F 2/2412* (2013.01);
(Continued)

(58) Field of Classification Search
CPC ................................. A61F 2/24; A61F 2/2418
See application file for complete search history.

(56) References Cited

U.S. PATENT DOCUMENTS 3,320,972 A 5/1967 High et al.
4,372,743 A 2/1983 Lane
(Continued)

FOREIGN PATENT DOCUMENTS

EP 2599858 A2 6/2013
JP S61185264 A 8/1986
(Continued)

OTHER PUBLICATIONS

Agarwal et al., "Interventional Cardiology Perspective of Functional Tricuspid Regurgitation", Circ Cardiovasc Interv, 2009, pp. 565-573, vol. 2.
(Continued)

*Primary Examiner* — Christopher D. Prone
(74) *Attorney, Agent, or Firm* — The Webb Law Firm

(57) ABSTRACT

An atrioventricular prosthesis device is provided. The device includes a frame at least partially defining and enclosing a central cavity, the frame having a distal portion, a proximal portion, and a middle portion connected therebetween. The device further includes a valve construct formed, at least in part, from a cell growth scaffold, at least partially disposed within the central cavity defined by the frame. The valve construct includes: an annular portion defining an aperture and being connected to the frame for positioning the valve construct within the central cavity of the frame, and a plurality of leaflets extending longitudinally
(Continued)

and radially inward from the annular portion. The frame and valve construct are transitionable to a deployed state, in which a diameter of at least a portion of the frame and the valve construct substantially conform to a diameter of a tricuspid and/or mitral valve opening.

20 Claims, 13 Drawing Sheets

Related U.S. Application Data continuation of application No. 15/553,811, filed as application No. PCT/US2016/019849 on Feb. 26, 2016, now Pat. No. 10,583,004.

(60) Provisional application No. 62/121,908, filed on Feb. 27, 2015, provisional application No. 62/126,040, filed on Feb. 27, 2015.

(51) Int. Cl.

| | |
|---|---|
| *A61L 27/50* | (2006.01) |
| *A61M 25/09* | (2006.01) |
| *A61N 1/362* | (2006.01) |
| *A61F 2/95* | (2013.01) |

(52) U.S. Cl.
CPC .............. *A61F 2/243* (2013.01); *A61L 27/14* (2013.01); *A61L 27/50* (2013.01); *A61M 25/09* (2013.01); *A61N 1/3629* (2017.08); *A61F 2002/9505* (2013.01); *A61F 2210/0019* (2013.01); *A61F 2240/001* (2013.01); *A61F 2250/001* (2013.01); *A61F 2250/0059* (2013.01); *A61L 2400/16* (2013.01)

(56) References Cited

U.S. PATENT DOCUMENTS

| | | | |
|---|---|---|---|
| 4,902,508 | A | 2/1990 | Badylak et al. |
| 4,956,178 | A | 9/1990 | Badylak et al. |
| 5,281,422 | A | 1/1994 | Badylak et al. |
| 5,352,463 | A | 10/1994 | Badylak et al. |
| 5,372,821 | A | 12/1994 | Badylak et al. |
| 5,554,389 | A | 9/1996 | Badylak et al. |
| 5,573,784 | A | 11/1996 | Badylak et al. |
| 5,645,860 | A | 7/1997 | Knapp, Jr. et al. |
| 5,753,267 | A | 5/1998 | Badylak et al. |
| 5,762,966 | A | 6/1998 | Knapp, Jr. et al. |
| 5,866,414 | A | 2/1999 | Badylak et al. |
| 6,099,567 | A | 8/2000 | Badylak et al. |
| 6,245,105 | B1 | 6/2001 | Nguyen et al. |
| 6,458,153 | B1 | 10/2002 | Bailey et al. |
| 6,485,723 | B1 | 11/2002 | Badylak et al. |
| 6,576,265 | B1 | 6/2003 | Spievack |
| 6,579,538 | B1 | 6/2003 | Spievack |
| 6,696,270 | B2 | 2/2004 | Badylak et al. |
| 6,783,776 | B2 | 8/2004 | Spievack |
| 6,793,939 | B2 | 9/2004 | Badylak |
| 6,849,273 | B2 | 2/2005 | Spievack |
| 6,852,339 | B2 | 2/2005 | Spievack |
| 6,861,074 | B2 | 3/2005 | Spievack |
| 6,887,495 | B2 | 5/2005 | Spievack |
| 6,890,562 | B2 | 5/2005 | Spievack |
| 6,890,563 | B2 | 5/2005 | Spievack |
| 6,890,564 | B2 | 5/2005 | Spievack |
| 6,893,666 | B2 | 5/2005 | Spievack |
| 7,041,132 | B2 | 5/2006 | Quijano et al. |
| 7,112,293 | B2 | 9/2006 | Dubson et al. |
| 7,175,656 | B2 | 2/2007 | Khairkhahan |
| 7,276,271 | B2 | 10/2007 | Dubson et al. |
| 7,455,689 | B2 | 11/2008 | Johnson |
| 7,611,534 | B2 | 11/2009 | Kapadia et al. |
| 7,803,184 | B2 | 9/2010 | McGuckin, Jr. et al. |
| 7,914,569 | B2 | 3/2011 | Nguyen et al. |
| 7,993,394 | B2 | 8/2011 | Hariton et al. |
| 8,080,054 | B2 | 12/2011 | Rowe |
| 8,361,503 | B2* | 1/2013 | Badylak .................. A61L 27/54 |
| | | | 424/572 |
| 8,470,023 | B2 | 6/2013 | Eidenschink et al. |
| 8,475,525 | B2 | 7/2013 | Maisano et al. |
| 8,623,079 | B2 | 1/2014 | Savage et al. |
| 2002/0090725 | A1* | 7/2002 | Simpson .............. D01D 5/0038 |
| | | | 623/23.72 |
| 2003/0114913 | A1 | 6/2003 | Spenser et al. |
| 2005/0075725 | A1 | 4/2005 | Rowe |
| 2006/0253192 | A1* | 11/2006 | Atala .................... A61F 2/2415 |
| | | | 623/2.13 |
| 2007/0269481 | A1 | 11/2007 | Li et al. |
| 2008/0009830 | A1* | 1/2008 | Fujimoto ................ A61L 31/06 |
| | | | 604/522 |
| 2008/0109070 | A1 | 5/2008 | Wagner et al. |
| 2008/0131965 | A1 | 6/2008 | Baaijens |
| 2008/0154358 | A1 | 6/2008 | Tansley et al. |
| 2008/0243245 | A1 | 10/2008 | Thambar et al. |
| 2008/0260831 | A1 | 10/2008 | Badylak et al. |
| 2008/0268019 | A1 | 10/2008 | Badylak et al. |
| 2009/0038761 | A1 | 2/2009 | Seddon |
| 2010/0249922 | A1 | 9/2010 | Li et al. |
| 2011/0082545 | A1 | 4/2011 | Freund |
| 2012/0059454 | A1 | 3/2012 | Millwee et al. |
| 2012/0101572 | A1 | 4/2012 | Kovalsky et al. |
| 2012/0136430 | A1 | 5/2012 | Sochman et al. |
| 2012/0172981 | A1* | 7/2012 | DuMontelle .......... A61F 2/2412 |
| | | | 623/2.17 |
| 2013/0035759 | A1 | 2/2013 | Gross et al. |
| 2014/0100653 | A1 | 4/2014 | Savage et al. |
| 2014/0128969 | A1 | 5/2014 | Hill et al. |
| 2014/0207250 | A1 | 7/2014 | O'Hare et al. |
| 2014/0243894 | A1 | 8/2014 | Groothuis et al. |

FOREIGN PATENT DOCUMENTS

| | | |
|---|---|---|
| JP | 2005507464 A | 3/2005 |
| JP | 2006158494 A | 6/2006 |
| JP | 2007522829 A | 8/2007 |
| JP | 2009524507 A | 7/2009 |
| WO | 2010041944 A1 | 4/2010 |
| WO | 2011106137 A1 | 9/2011 |
| WO | 2011150328 A1 | 12/2011 |
| WO | 2012024390 A2 | 2/2012 |
| WO | 2014007631 A1 | 1/2014 |
| WO | 2014066365 A1 | 5/2014 |
| WO | 2014138194 A1 | 9/2014 |

OTHER PUBLICATIONS

Agarwal et al., "Progress in the Field of Electrospinning for Tissue Engineering Applications", Adv. Mater., 2009, pp. 3343-3351, vol. 21.

Bloomfield et al., "Twelve-Year Comparison of a Bjork-Shiley Mechanical Heart Valve With Porcine Bioprostheses", The New England Journal of Medicine, 1991, pp. 573-579, vol. 324:9.

Bourke et al., "Polymers derived from the amino acid L-tyrosine: polycarbonates, polyarylates and copolymers with poly(ethylene glycol)", Advanced Drug Delivery Reviews, 2003, pp. 447-466, vol. 55.

Bryan et al., "Prospective randomized comparison of CarboMedics and St. Jude Medical bileaflet mechanical heart valve prostheses: Ten-year follow-up", J Thorac Cardiovasc Surg, 2007, pp. 614-622, vol. 133.

Cobanoglu et al., "Aortic Valve Replacement with the Starr-Edwards Prosthesis: A Comparison of the First and Second Decades of Follow-up", Ann Thorac Surg; 1988; pp. 248-252; vol. 45.

Del Gaudio et al., "Electrospun bioresorbable heart valve scaffold for tissue engineering", The International Journal of Artificial Organs, 2008, pp. 68-75, vol. 31:1.

Fiordeliso et al., "Design, synthesis, and preliminary characterization of tyrosine-containing polyarylates: New biomaterials for medical applications", J. Biomater. Sci. Polymer Edn, 1994, pp. 497-510; vol. 5:6.

(56) References Cited

OTHER PUBLICATIONS

Fujimoto et al., "An Elastic, Biodegradable Cardiac Patch Induces Contractile Smooth Muscle and Improves Cardiac Remodeling and Function in Subacute Myocardial Infarction", J Am Coll Cardiol, 2007, pp. 2292-2300, vol. 49.

Gallegos et al., "In-Vivo Experience with the Triflo Trileaflet Mechanical Heart Valve", The Journal of Heart Valve Disease, 2006, pp. 791-799, vol. 15.

Gregoric et al., "Preclinical Hemodynamic Assessment of a New Trileaflet Mechanical Valve in the Aortic Position in a Bovine Model", The Journal of Heart Valve Disease, 2004, pp. 254-259; vol. 13.

Guan et al., "Synthesis, characterization, and cytocompatibility of elastomeric, biodegradable poly(ester-urethane)ureas based on poly(caprolactone) and putrescine", J Biomed Mater Res, 2002, pp. 493-503, vol. 61.

Hashizume et al., "Morphological and mechanical characteristics of the reconstructed rat abdominal wall following use of a wet electrospun biodegradable polyurethane elastomer scaffold", Biomaterials, 2010, pp. 3253-3265, vol. 31.

Hong et al., "Tailoring the degradation kinetics of poly(ester carbonate urethane)urea thermoplastic elastomers for tissue engineering scaffolds", Biomaterials, 2010, pp. 4249-4258, vol. 31.

Huang et al., "A Library of L-Tyrosine-Derived Biodegradable Polyarylates for Potential Biomaterial Applications, Part I: Synthesis, Characterization and Accelerated Hydrolytic Degradation", Journal of Biomaterials Science, 2009, pp. 935-955, vol. 20.

Kidane et al., "Review Current Developments and Future Prospects for Heart Valve Replacement Therapy", J Biomed Mater Res Part B: Appl Biomater, 2009, pp. 290-303, vol. 88B.

Koens, "Part I: From a parameterized computer model of the aortic valve to a stentless 3D scaffold and functional evaluation", Nov. 19, 2004, 14 pages.

Lee et al., "Nanofiber alignment and direction of mechanical strain affect the ECM production of human ACL fibroblast", Biomaterials, 2005, pp. 1261-1270, vol. 26.

Mirnajafi et al., "The flexural rigidity of the aortic valve leaflet in the commissural region", Journal of Biomechanics, 2006, pp. 2966-2973, vol. 39.

Morsi et al., "Current Developments and Future Challenges for the Creatin of Aortic Heart Valve", Journal of Mechanics in Medicine and Biology, 2008, pp. 1-15, vol. 8:1.

O'Brien et al., "Allograft Aortic Valve Replacement: Long-Term Follow-up", Ann Thorac Surg, 1995, pp. S65-S70, vol. 60.

Rogers, "Functional Tricuspid Regurtitation Percutaneous Therapies Needed", Jacc: Cardiovascular Interventions, 2015, 3 pages.

Rogers et al., "Transatrial Intrapericardial Tricuspid Annuloplasty", Jacc: Cardiovascular Interventions, 2015, 9 pages.

Sacks, "Biaxial Mechanical Evaluation of Planar Biological Materials", Journal of Elasticity, 2000, pp. 199-246, vol. 61.

Sacks et al., "Collagen fiber disruption occurs independent of calcification in clinically explanted bioprosthetic heart valves", J Biomed Mater Res, 2002, pp. 359-371, vol. 62.

Schoen et al., "Tissue Heart Valve: Current Challenges and Future Research Perspectives", J Biomed Mater Res, 1999, pp. 439-465, vol. 47.

Schoen et al., "Calcification of Tissue Heart Valve Substitutes: Progress Toward Understanding and Prevention", Ann Thorac Surg, 2005, pp. 1072-1080, vol. 79.

Schoevaerdts et al., "Twenty years' experience with the Model 6120 Starr-Edwards valve in the mitral position", J Thorac Cardiovasc Surg, 1987, pp. 375-382, vol. 94.

Simonet et al., "Heart valve tissue regeneration", 2011, pp. 202-224.

Simonet et al., "Hemodynamic testing of a 3D electrospun heart valve prosthesis", 2011, 2 pages.

Soletti et al., "A bilayered elastomeric scaffold for tissue engineering of small diameter vascular grafts", Acta Biomaterialia, 2010, pp. 110-122, vol. 6.

Stankus et al., "Hybrid nanofibrous scaffolds from electrospinning of a synthetic biodegradable elastomer and urinary bladder matrix", J Biomater Sci Polym Ed, 2008, pp. 635-652, vol. 19:5.

Van Lieshout et al., "Electrospinning versus knitting: two scaffolds for tissue engineering of the aortic valve", J. Biomater. Sci. Polymer Edn, 2006, pp. 77-89, vol. 17:1-2.

Vongpatanasin et al., "Prosthetic Heart Valves", The New England Journal of Medicine, 1996, pp. 407-416, vol. 335:6.

Wells et al., "Cyclic loading response of bioprosthetic heart valves: effects of fixation stress state on the collagen fiber architecture", Biomaterials, 2005, pp. 2611-2619, vol. 26.

Wu et al., "Mechanical heart valves: Are two leaflets better than one", J Thorac Cardiovasc Surg, 2004, pp. 1171-1179, vol. 127.

Xu et al., "Aligned biodegradable nanofibrous structure: a potential scaffold for blood vessel engineering", Biomaterials, 2004, pp. 877-886, vol. 25.

Yacoub et al., "Fourteen-Year Experience With Homovital Homografts for Aortic Valve Replacement", J Thorac Cardiovasc Surg, 1995, pp. 186-194, vol. 110.

* cited by examiner

RETRIEVABLE SELF-EXPANDING NON-THROMBOGENIC LOW-PROFILE PERCUTANEOUS ATRIOVENTRICULAR VALVE PROSTHESIS

CROSS REFERENCE TO RELATED APPLICATIONS

This application is a continuation of U.S. patent application Ser. No. 16/777,007, filed Jan. 30, 2020, which issued as U.S. Pat. No. 11,771,555 on Oct. 3, 2023, which is a continuation of U.S. patent application Ser. No. 15/553,811, filed Aug. 25, 2017, which issued as U.S. Pat. No. 10,583,004 on Mar. 10, 2020, which is a national stage of International Patent Application No. PCT/US2016/019849, filed Feb. 26, 2016, which claims the benefit of United States Patent Provisional Application Ser. Nos. 62/121,908 and 62/126,040, filed Feb. 27, 2015, each of which is hereby incorporated by reference in its entirety.

BACKGROUND OF THE INVENTION

Field of the Invention

The present disclosure is generally directed to an implantable and removable valve prosthesis device and, more particularly, to an atrioventricular valve prosthesis device configured for implantation adjacent to a mitral or tricuspid valve of a patient and having a polymer valve structure mounted to a flexible and compressible frame.

Description of Related Art

Heart valve disease is a condition in which one or more of the valves between heart chambers of a patient malfunction. In adults, valvular heart disease continues to be a major cause of morbidity and mortality with approximately 60,000 valve replacements performed in the United States in 2013. This number does not include transcatheter aortic valve replacements (TAVR) and open surgical valve replacements. About 2,000 TAVR procedures are performed per year. About 1,000 open surgical tricuspid valve replacements are performed each year. The reported number of valve replacements in the United States also does not include mitral and tricuspid surgical repairs, which were approximately 25,000 in 2013.

There are typically two types of prosthetic heart valve replacements, namely mechanical and bioprosthetic valve replacements. Generally, mechanical heart valves are made entirely of synthetic materials, such as metals and pyrolytic carbon polymers. Bioprosthetic heart valves are made from tissue from animals (e.g., bovine, porcine, or equine) or from human tissue. Mechanical heart valves are very durable and may last decades. However, these valves may have limited central flow due to their designs, such as bileaflet or tilting disc mechanisms.

In addition, one of the major drawbacks of mechanical heart valves is the requirement of the daily anticoagulant warfarin due to an increased risk of artificial material induced thrombosis and thromboembolism. Bioprosthetic heart valves have improved central blood flow due to their biomimicking trileaflet design and do not generally require anticoagulant therapy. However, bioprosthetic heart valves also have some drawbacks including limited durability due to leaflet calcification, leaflet tearing, fatigue damage, and tissue failure. Therefore, 10 to 20 percent of homograft bioprostheses and 30 percent of heterograft bioprostheses fail within 10 to 15 years of implantation and require re-replacement.

Both mechanical and bioprosthetic heart valves require open heart surgery assisted with cardiopulmonary bypass. Until recently, there were few options for patients believed to be too high risk to undergo major open surgery. The development of percutaneous heart valve replacement has coincided with the development of novel biomaterials and innovative treatment strategies to address these high risk patients.

Percutaneous heart valve replacement is an emerging technology with few commercially available devices. Available devices for percutaneously delivering a prosthetic valve may not be suitable for tricuspid valve or mitral valve (atrioventricular) replacement due to complex anatomy and relatively fragile surrounding tissues. For example, a known percutaneous solution for symptomatic tricuspid regurgitation is off-label use of a balloon-expandable aortic prosthesis in the superior vena cava (SVC) and inferior vena cava (IVC). Such procedures have had varied and anecdotal success. However, most stented bioprosthetic valves are not feasible for tricuspid valve replacement because the deployed stent backbone may disturb the architecture of the right ventricular outflow tract and the atrioventricular node located adjacent to tricuspid valve leaflets. In addition, existing percutaneous devices are dependent on radial force to anchor the device. This radial force-dependent mechanism may not be preferable for positioning and holding the valve in the tricuspid valve region because there is insufficient fibrous support to apply radial force anchoring, which creates a risk of annular disruption, as well as atrioventricular nodal compression and heart block.

SUMMARY OF THE INVENTION

To address these issues, a self-expanding percutaneous tricuspid valve that is non-thrombogenic, durable, and low-profile, is provided herein. The device can be easily delivered and securely placed in the tricuspid valve region. The approach described herein further mitigates concerns regarding heart block.

In some aspects, the device comprises a highly-elastic self-expanding shape-memory superelastic (e.g., nitinol) frame and a single-body tri-leaflet or bi-leaflet valve construct that is precisely tailored in its mechanical properties to mimic natural valve behavior. In some aspects, the device is percutaneously inserted via the venous system to access either the SVC or IVC with preference of simplicity given to subclavian or internal jugular venous access. In another aspect, the device is deployed over a guiding rail, the distal aspect of which is anchored temporarily or permanently, in the case of the tricuspid valve, to the right ventricular endocardium. In yet another aspect, the device is deployed over a pacemaker lead, facilitating either co-employment or later employment of a pacemaker generator for ventricular pacing.

The device described herein is designed to be placed over existing native tricuspid valve or mitral valve tissue without resection. It may, however, be used in the setting of prior tricuspid or mitral surgery as a valve-in-valve procedure in a degenerative surgical tissue valve, or a valve-in-ring procedure after failed tricuspid or mitral annuloplasty ring repair. It can also be used in the setting of a prior pacemaker or defibrillator lead placement and lead-related functional tethering of the triscuspid leaflet.

In another aspect, a mitral valve prosthetic device is provided. In one aspect, the mitral valve device is deployed by a percutaneous mitral transseptal approach, more specifically, percutaneously with transseptal access to the left atrium and delivery across the mitral valve with anchoring in the left ventricle, holding the device in place in the mitral position. As with the tricuspid valve prosthesis, a rail guide with ventricular anchoring may be used to anchor the device and position it within the mitral valve annulus.

In another aspect, an atrioventricular prosthesis device is provided. The device comprises: a frame disposed on a central member extending along a longitudinal axis thereof, and at least partially defining and enclosing a central cavity, the frame having a distal portion, a proximal portion, and a middle portion connected therebetween; and a valve construct formed, at least in part, from a cell growth scaffold, at least partially disposed within the central cavity defined by the frame. The valve construct comprises: an annular portion defining an aperture and being connected to the frame for positioning the valve construct within the central cavity of the frame, and a plurality of leaflets extending longitudinally and radially inward from the annular portion. The frame and valve construct are transitionable from a contracted state, in which the frame and valve construct are configured to be disposed within a catheter tube, and a deployed state in which a diameter of at least a portion of the frame and the valve construct substantially conforms to a diameter of a tricuspid and/or mitral valve opening.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

DESCRIPTION OF THE INVENTION

Figure 1A:
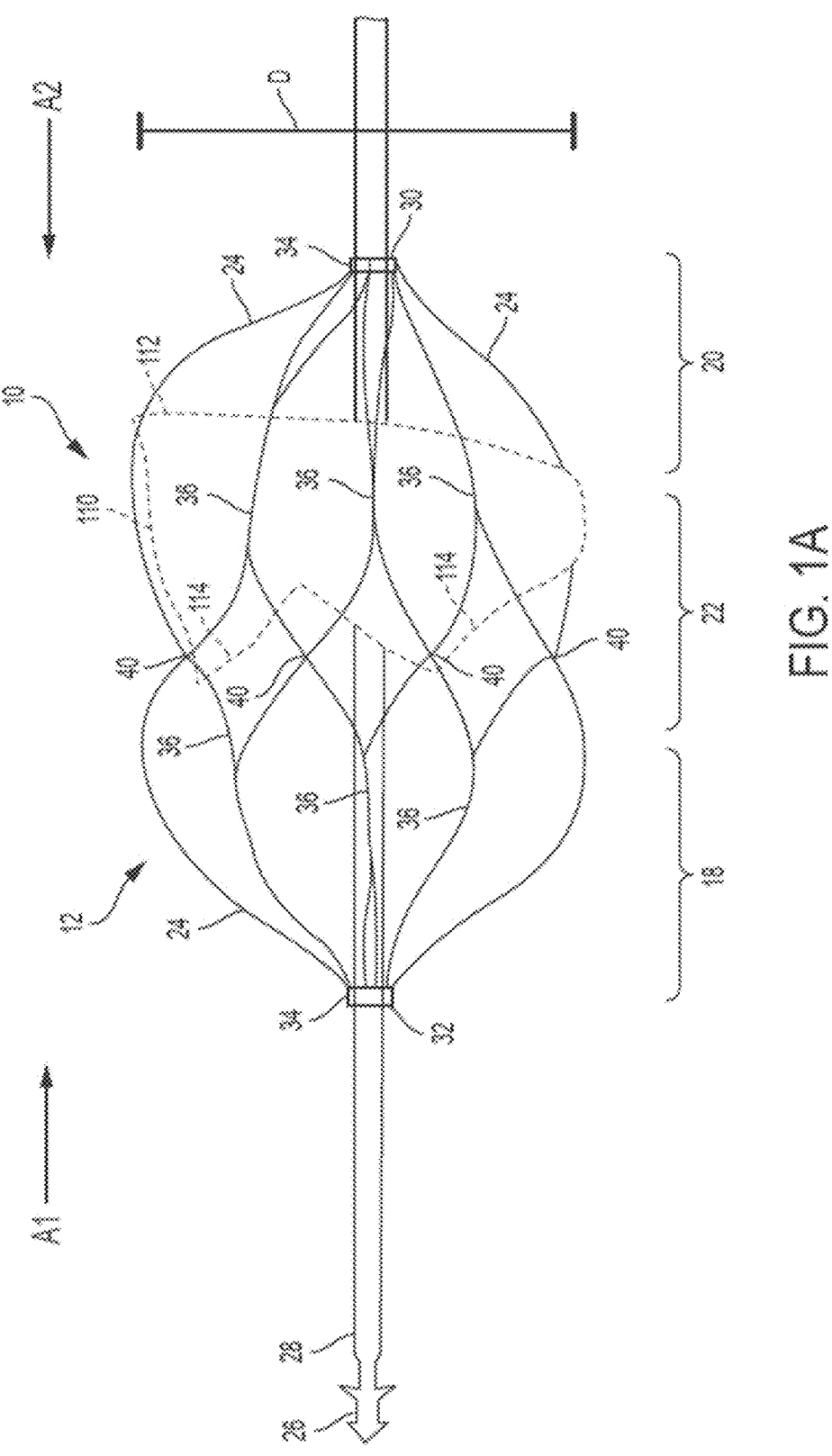
FIG. 1A is a front view of an embodiment of an atrioventricular prosthesis device in a deployed state, according to an aspect of the invention.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the terms "comprising," "comprise" or "comprised," and variations thereof, are meant to be open ended. The terms "a" and "an" are intended to refer to one or more.

As used herein, the "treatment" or "treating" of a condition, wound, or defect means administration to a patient by any suitable dosage regimen, procedure and/or administration route of a composition, device or structure with the object of achieving a desirable clinical/medical end-point, including repair and/or replacement of a tricuspid or mitral valve.

As used herein, the term "patient" or "subject" refers to members of the animal kingdom including but not limited to human beings and "mammal" refers to all mammals, including, but not limited to human beings.

A polymer composition is "biocompatible" in that the polymer and, where applicable, degradation products thereof, are substantially non-toxic to cells or organisms within acceptable tolerances, including substantially non-carcinogenic and substantially non-immunogenic, and are cleared or otherwise degraded in a biological system, such as an organism (patient) without substantial toxic effect. Non-limiting examples of degradation mechanisms within a biological system include chemical reactions, hydrolysis reactions, and enzymatic cleavage.

As used herein, the term "polymer composition" is a composition comprising one or more polymers. As a class, "polymers" includes, without limitation, homopolymers, heteropolymers, co-polymers, block polymers, block co-polymers and can be both natural and/or synthetic. Homopolymers contain one type of building block, or monomer, whereas copolymers contain more than one type of monomer. The term "(co)polymer" and like terms refer to either homopolymers or copolymers.

A polymer "comprises" or is "derived from" a stated monomer if that monomer is incorporated into the polymer. Thus, the incorporated monomer (monomer residue) that the polymer comprises is not the same as the monomer prior to incorporation into a polymer, in that at the very least, certain groups are missing and/or modified when incorporated into the polymer backbone. A polymer is said to comprise a specific type of linkage if that linkage is present in the polymer.

As described herein, a "fiber" an elongated, slender, thread-like and/or filamentous structure. A "matrix" is any two- or three-dimensional arrangement of elements (e.g., fibers), either ordered (e.g., in a woven or non-woven mesh) or randomly-arranged (as is typical with a mat of fibers typically produced by electrospinning) and can be isotropic or anisotropic.

By "biodegradable or "bioerodable", it is meant that a polymer, once implanted and placed in contact with bodily fluids and tissues, will degrade either partially or completely through chemical reactions with the bodily fluids and/or tissues, typically and often preferably over a time period of hours, days, weeks or months. Non-limiting examples of such chemical reactions include acid/base reactions, hydrolysis reactions, and enzymatic cleavage. The biodegradation rate of the polymer matrix may be manipulated, optimized or otherwise adjusted so that the matrix degrades over a useful time period. The polymer or polymers typically will be selected so that it degrades in situ over a time period to optimize mechanical conditioning of the tissue. For instance, in the case of abdominal wall repair, it is desirable that the matrix dissolves over at least a week and preferably longer. More importantly, the matrix would have to retain its supportive capacity until tissue remodeling occurs, such as for at least 2-8 weeks, or longer.

FIGS. 1A, 1B, 2, and 3 depict one aspect of an atrioventricular prosthesis device 10. Device 10 generally comprises a frame 12 disposed on a central member 14, such as a catheter tube, catheter guiderail, and/or a pacemaker lead (electrode), extending along a longitudinal axis L thereof. The frame 12 defines and at least partially encloses a central cavity 16. The frame 12 comprises a distal portion 18, a proximal portion 20, and a middle portion 22 connected therebetween. The device 10 further comprises a valve construct 110 formed, at least in part, from a cell growth scaffold, such as a biodegradable and biocompatible polymer material. The valve construct 110 is at least partially disposed within the central cavity 16. The valve construct 110 comprises a support or annular portion 112 (forming a ring, but not necessarily defining any particular geometric shape such as a circle or cylinder) connected to the frame 12 for positioning the valve construct 110 within the central cavity 16 of the frame 12. The valve construct 110 further comprises a plurality of leaflets 114 extending longitudinally and radially inward from the annular portion 112. In some examples, the valve construct 110 includes three leaflets 114 arranged to correspond to the structure of a tricuspid valve. In another example, the valve construct 110 comprises two leaflets 114 arranged to correspond to the structure of a mitral (bicuspid) valve.

Figure 1B:
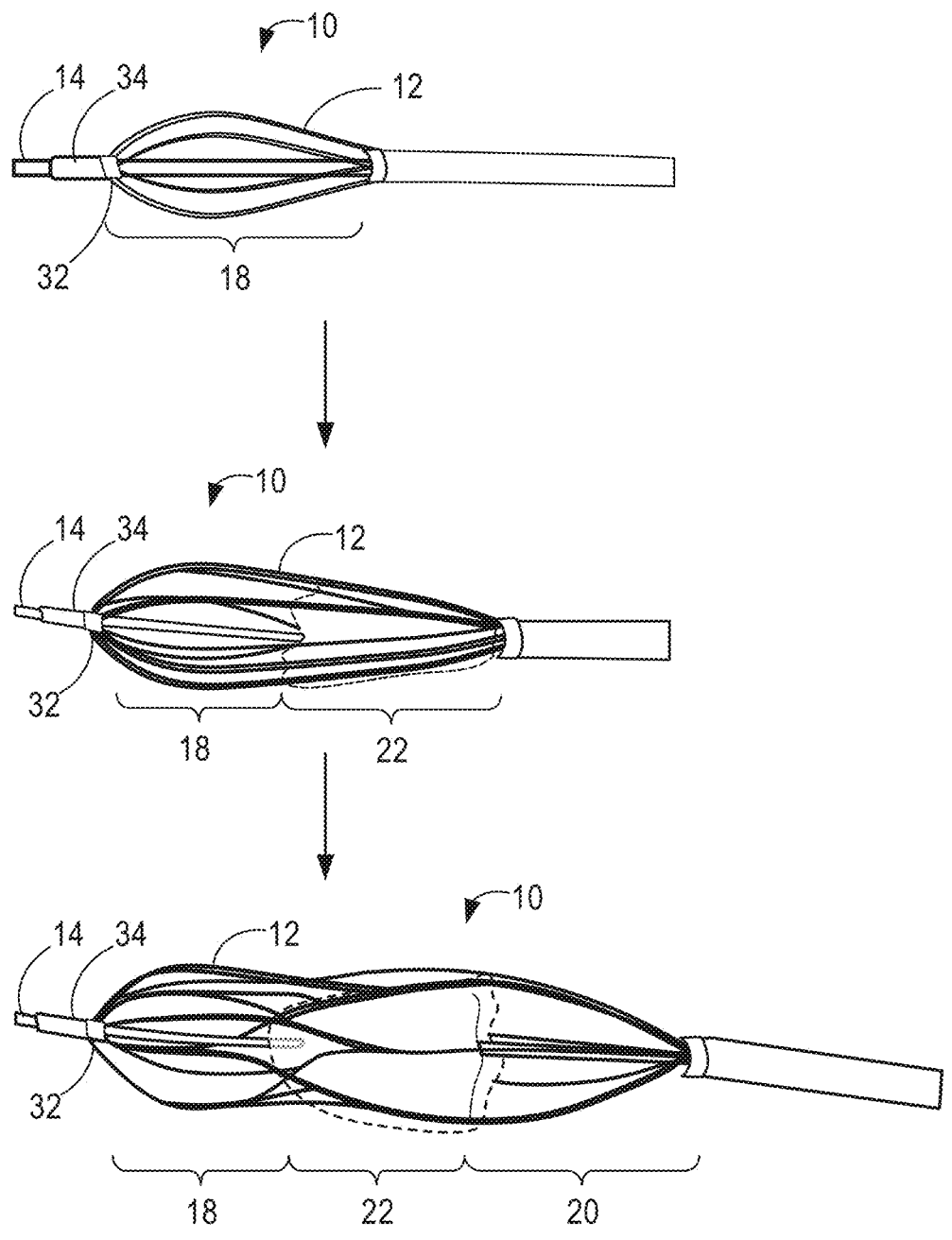
FIG. 1B is a sequence of photographs of the atrioventricular prosthesis device of FIG. 1A in a collapsed state and being deployed from a catheter tube.
Figure 2:
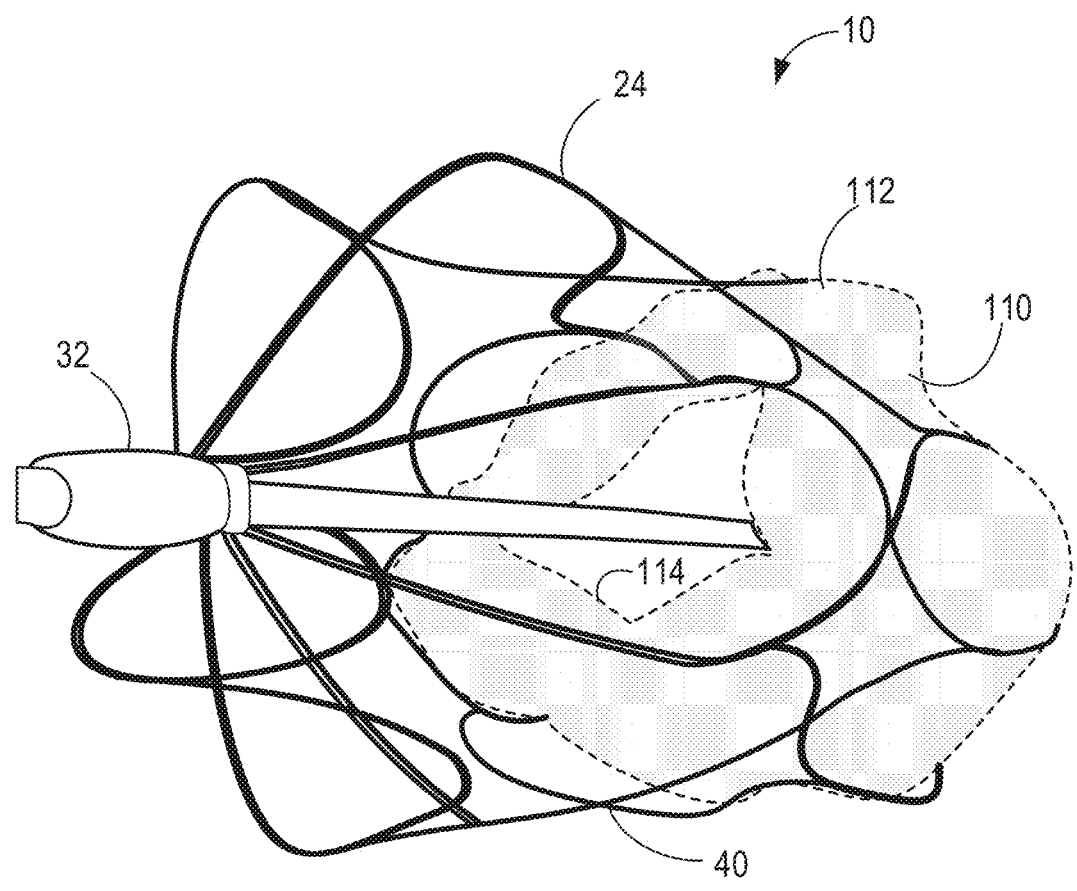
FIG. 2 is a photograph of a perspective view of a distal portion of the atrioventricular prosthesis device of FIG. 1A.
Figure 3:
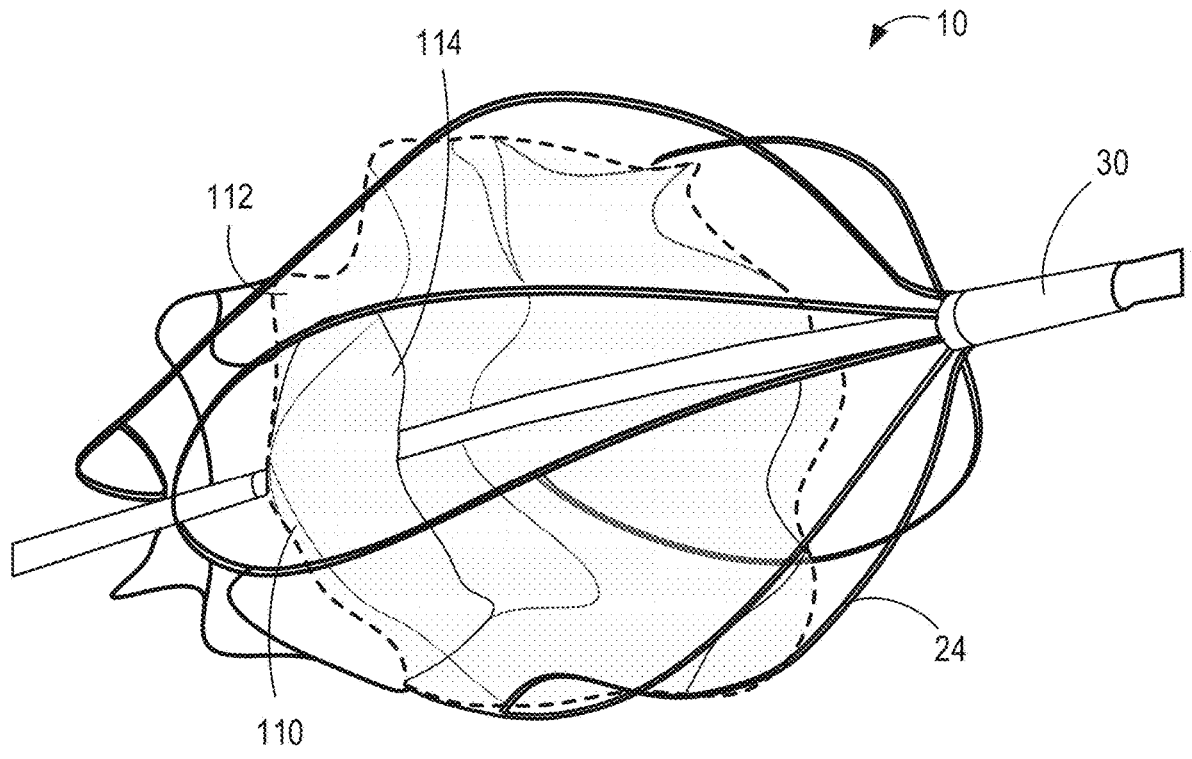
FIG. 3 is a photograph of a perspective view of a proximal portion of the atrioventricular prosthesis device of FIG. 1A.

The frame 12 and valve construct 110 are transitionable from a contracted state, shown, for example, in FIG. 1B, in which the frame 12 and valve construct 110 are collapsed to be disposed within a catheter tube, and a deployed state, shown in FIG. 1A, in which a diameter D of at least a portion of the frame 12 and/or of the annular portion 112 of the valve construct 110 substantially conforms to a dimeter of a tricuspid and/or mitral valve opening of a patient.

Exemplary Frame:

With specific reference to FIG. 1A, the frame 12 comprises a plurality of elongated members 24 extending from and disposed substantially symmetrically about the central member 14.

In some embodiments, the members 24 comprise a super-elastic shape-memory material, such as Nitinol. Nitinol is a nickel titanium allow that has found broad use in a wide range of trans-catheter devices due to its shape memory property. The shape memory response is defined as a mechanical deformation in a low temperature state (martensite) with deformations fully recovered when the material is heated to body temperature (austenite). This shape memory behavior is useful for trans-catheter devices because Nitinol structures can easily be collapsed into a small diameter catheter in its martensite phase. Upon exposure to blood temperature, the Nitinol structure deploys spontaneously to its original shape (the austenite phase). Therefore, as a result of its material construction, upon warming to blood temperature, the frame 12 self-expands from its collapsed state to the deployed state. Because the magnitude of its recoverable deformation of Nitinol is much greater than elastic deformation of metals such as surgical steel, Nitinol-based devices can be placed into small diameter catheters for a wide range of catheter-based procedures. Additional suitable super-elastic shape-memory alloys, such as cobalt chromium alloys, are also useful for this purpose, as are broadly known in the stenting and aneurysm device fields.

As shown in FIG. 1A, in some aspects, to accommodate changes in longitudinal length of the frame 12 during compression or expansion thereof, the frame 12 includes a tube or collar 34 slidably disposed about the central member 14. Optionally, the collar 34 is positioned at the distal end 32 of the frame 12. The elongated members 24 of the frame 12 are connected to and/or extend from the collar 34 and are attached directly to the central member 14 at the proximal end 30 thereof. To transition the frame 12 to its deployed state, the proximal end 30 of the frame 12 is advanced longitudinally, in the direction of arrow A2. As the proximal end 30 is advanced in the distal direction A1, the collar 34 slides along the central member 14 in a proximal direction, as shown by arrow A1, thereby allowing the frame 12 to shorten longitudinally, such that the diameter increases to a deployed diameter D suitable for the tricuspid or mitral valve opening. Likewise, when the frame 12 lengthens upon compression, the collar 34 slides in the distal direction along the central member 14, shown by arrow A2. Optionally, the distal collar 34 is sufficiently tight on the central member 14 to produce a degree of friction between the collar 34 and the central member 14 to prevent the collar 34 from sliding until a sufficient contracting or expanding force is exerted on the collar 34 by the frame 12.

In another example, the elongated members 24 are fixedly connected to the central member 14 at both the proximal end 30 and the distal end 32 of the frame 12. In that case, the elongated members 24 may include joints or bends to accommodate expansion of the frame 12 to its deployed position without substantially altering the longitudinal length thereof.

In yet another example, the frame 12 comprises a collar 34 at each of the distal end 32 and the proximal end 30 thereof to allow for a greater degree of expansion and/or contraction of the frame 12 relative to the central member 14. In one aspect, a frame 12 having collars 34 at each end thereof is used with a pacemaker lead as the central member 14. When used in connection with a pacemaker lead, the device 10 and the frame 12 are advanced along the lead by sliding the collars 34 over the lead until a desired position adjacent to a mitral or tricuspid valve is reached. Once at the desired position, the collar 34 at the distal end 32 of the frame 12 is fixed to the lead (e.g., the central member 14). In some examples, the collar 34 is fixed by actuating a mechanical clamp located on an interior surface of the collar 34. While the collar 34 at the distal end 32 of the frame 12 is fixed to the pacemaker lead, the collar 34 at the proximal end 30 of the frame 12 continues to advance in the distal direction, thereby causing the frame 12 to transition to its deployed state and expanded diameter D. Once the desired diameter D is obtained, the collar 34 on the proximal end 30 of the frame 12 is fixed to the pacemaker lead to maintain the device 10 in its deployed position. In some examples, the proximal collar 34 is fixed by actuating a mechanical clamp. As discussed in greater detail hereinafter, if the central member 14 and/or pacemaker lead is to be removed from the body, the proximal end 30 of the device 10 is disconnected from the central member 14 (e.g., guiderail or pacemaker lead) by releasing a connector or release mechanism that holds the frame 12 to the central member 14. The connector can be one or more of a screw type mechanism that is released by rotating the guidewire, a mechanical clamp, and/or suturing (e.g., using nylon threads).

With continued reference to FIG. 1A, in some aspects, the central member 14 comprises an anchor, such as a barb 26, positioned at least at a distal end 28 thereof. The barb 26 can be configured to anchor the central member 14 and device 10 in position and to maintain the position thereof by application of a longitudinal force. In some aspects, a pacemaker lead can further comprise a conductor, an insulating sheath, and an exposed conductor, at the distal end thereof. In that case, the barb 26 is used for anchoring the distal end 28 of the pacemaker lead to tissue, such into the endocardium. Barbs and barbed ends useful for anchoring the distal end 28 can have any useful configuration, variations of which are not shown, as one of ordinary skill in the art can readily envision any suitable barb configuration.

In some aspects, the elongated members 24 are arranged and/or bended to form a low density frame structure having enclosed portions or lattices extending around the circumference thereof. For example, as shown in FIG. 1A, the elongated members 24 of the proximal portion 20 are arranged as a plurality of wire pairs, in which each member 24 of a wire pair is attached to the other member 24 at a connection point 36 between the proximal end 30 and the middle portion 22 of the frame 12. At the middle portion 22, each member 24 is attached to a member 24 of a circumferentially adjacent wire pair to form a plurality of circumferentially disposed petal-shaped lattices having a tip 40 at the middle portion 22 of the frame 12. As shown in FIG. 1A, the distal portion 18 of the frame 12 is a mirror image of the proximal portion 20. Specifically, the distal portion 18 comprises a plurality of corresponding wire pairs attached to and extending longitudinally from the collar 34. The attached elongated members 24 extend in a generally longitudinal direction toward the middle portion 22 of the frame 12. Each member 24 of a wire pair is attached to the other at a connection point 36 between the distal end 32 of the frame 12 and the middle portion 22. At the middle portion 22, each member 34 is attached to a member 24 of a circumferentially adjacent wire pair 36 to form a plurality of circumferentially disposed petal shaped lattices having a tip 40 at the middle portion 22 where the members 24 from adjacent wire pairs 36 are joined.

As shown in FIG. 1A, the proximal portion 20 and the distal portion 18 of the frame 12 have the same number of wire pairs and tips 40. Further, the tips 40 of the distal portion 18 and the proximal portion 20 are circumferentially aligned. Accordingly, each tip 40 of each petal lattice of the proximal portion 20 is easily attached to an adjacent corresponding tip 40 of the distal portion 18 to form a contiguous frame structure. However, other collapsible geometries are contemplated and are possible, considering the vast number of self-expanding stent and aneurysm-repair device geometries known to those of ordinary skill in the art. For example, the frame 12 can have any of a variety of low density expanded structures suitable for insertion within a small diameter catheter and having a large expanded diameter that corresponds to a diameter of the tricuspid and mitral valves. A "low density structure" refers to a structure in which a volume of the elements that form the structure is substantially less than a volume of the structure (e.g., a volume defined between the inner surface and the outer surface of the frame 12). It also is desirable to avoid undue radial pressure on the existing valve annulus, which also favors a lower density structure.

Figure 4:
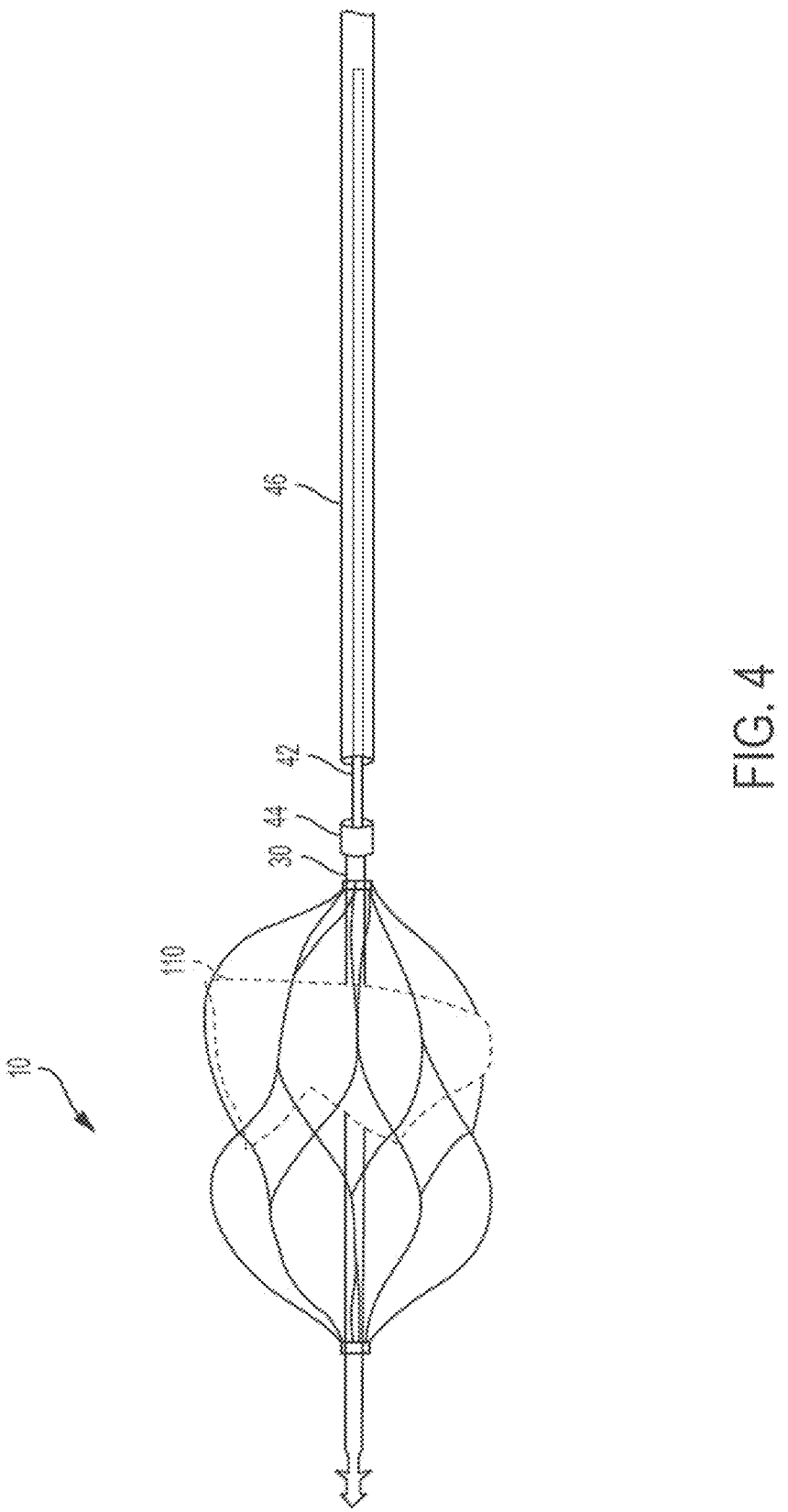
FIG. 4 is a front view of the atrioventricular prosthesis device of FIG. 1A mounted to a catheter tube for deployment and retrieval, according to an aspect of the invention.

Connector and/or Release Mechanism:

With reference to FIG. 4, an atrioventricular prosthesis device 10, catheter guiderail 42, and release mechanism 44 connecting the device 10 to the guiderail 42 are illustrated. In some aspects, the release mechanism 44 is a screw-type disconnection component that can be disconnected from the guiderail 42 by rotating the guiderail 42. The release mechanism 42 further comprises a secondary sheath 46 enclosing the guiderail 42. The secondary sheath 46 aids in disconnection of the guiderail 42 from the proximal end 30 of the device 10. Specifically, the secondary sheath 46 can be advanced in a distal direction to press against the device 10 to separate it from the guiderail 42. In use, in one non-limiting example, the device 10 is advanced along the guiderail 42 to a desired location. Once the device 10 is positioned in the desired location, it is expanded to its deployed state. The device 10 is then released from the guiderail 42 by rotating the guiderail 42 to release the screw-type disconnection component of the release mechanism 44. To aid in pushing the device 10 away from the guiderail 42, the secondary sheath 46 is advanced in the distal direction to push against the proximal end 30 of the device. Once the device 10 is released, the guiderail 42 can be removed from the deployment site and/or the body.

Figure 5A:
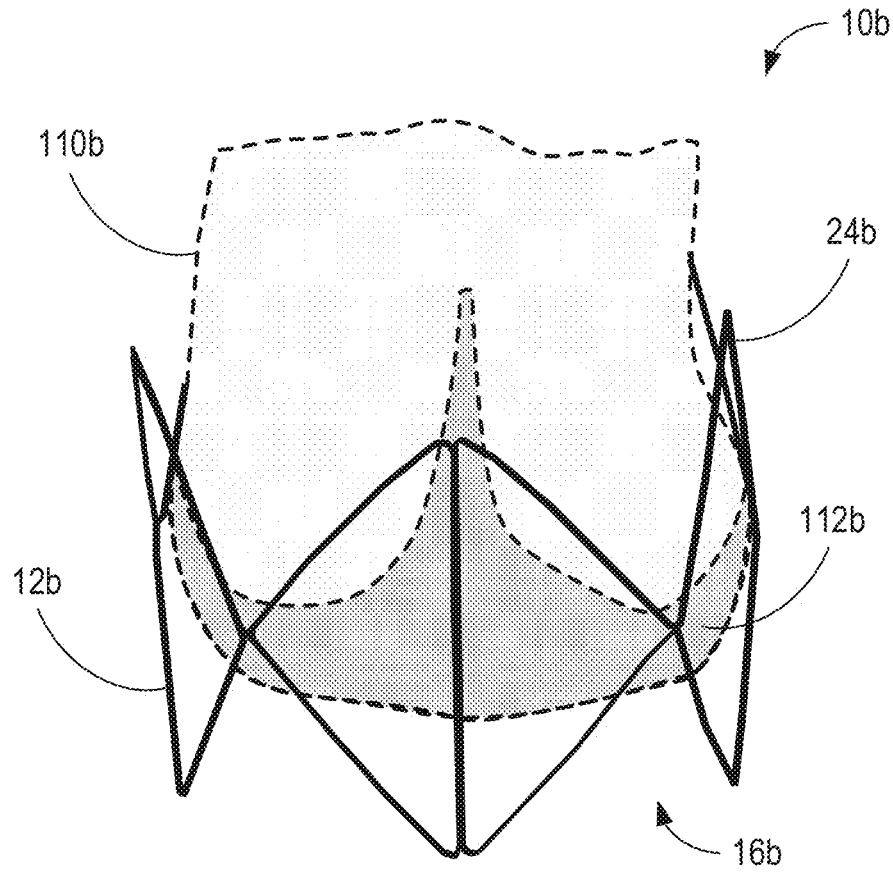
FIG. 5A is a photograph of a front view of another embodiment of an atrioventricular prosthesis device, in accordance with an aspect of the present invention.
Figure 5B:
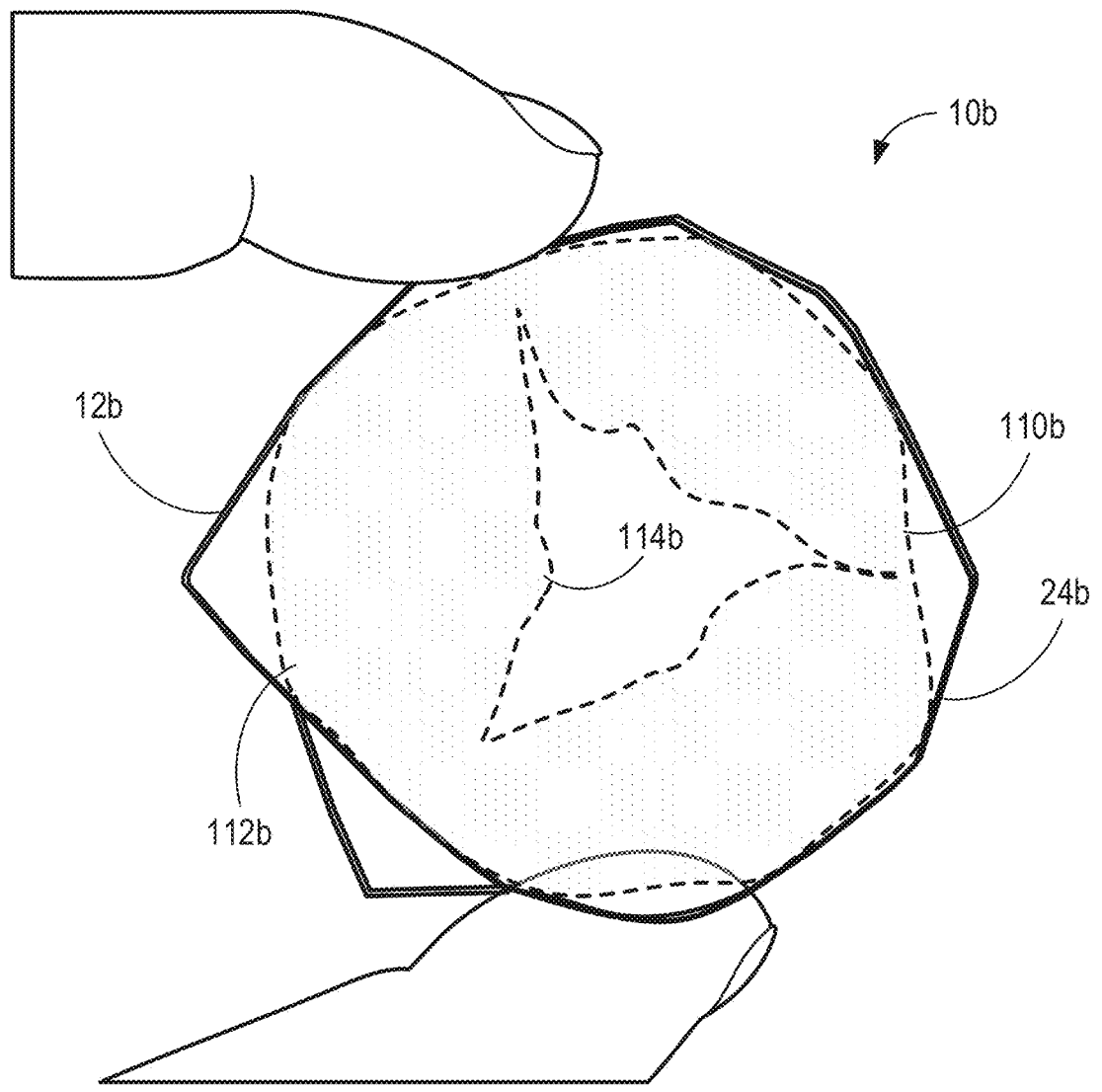
FIG. 5B is a photograph of a proximally directed side view of the atrioventricular prosthesis device of FIG. 5A.

Alternative Frame Examples:

With reference to FIGS. 5A and 5B, another aspect of a frame 12b for use with an atrioventricular prosthesis device 10b is illustrated. As in the previously described examples, the frame 12b comprises a plurality of elongated superelastic members 24b extending around and at least partially enclosing a central cavity 16b. Unlike in previously described aspects, the members 24b extend around a circumference of the cavity 16b, rather than in a longitudinal direction. A valve construct 110b is mounted to the frame 12b and at least partially enclosed within the cavity 16b. As shown in FIG. 5B, the valve construct 110b is configured to correspond in shape to a tricuspid valve. The valve construct 110b comprises a support or annular portion 112b that is connected at various points to the elongated members 24b of the frame 12b and three leaflets 114b extending radially and longitudinally inward from the annular portion 112b. Unlike the previously described examples, the frame 12b is not mounted to a central member.

Figure 6A:
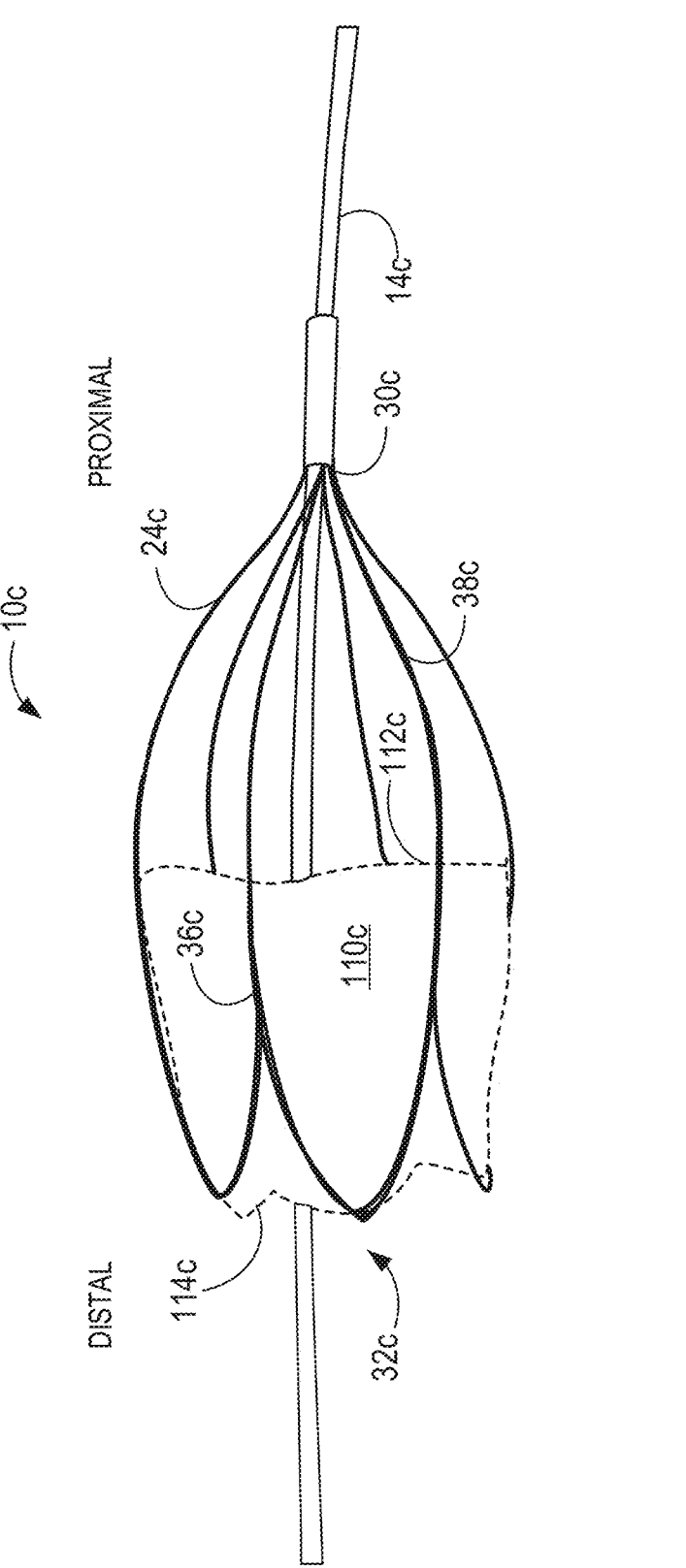
FIG. 6A is a photograph of a front view of another embodiment of an atrioventricular prosthesis device, in accordance with an aspect of the present invention.
Figure 6B:
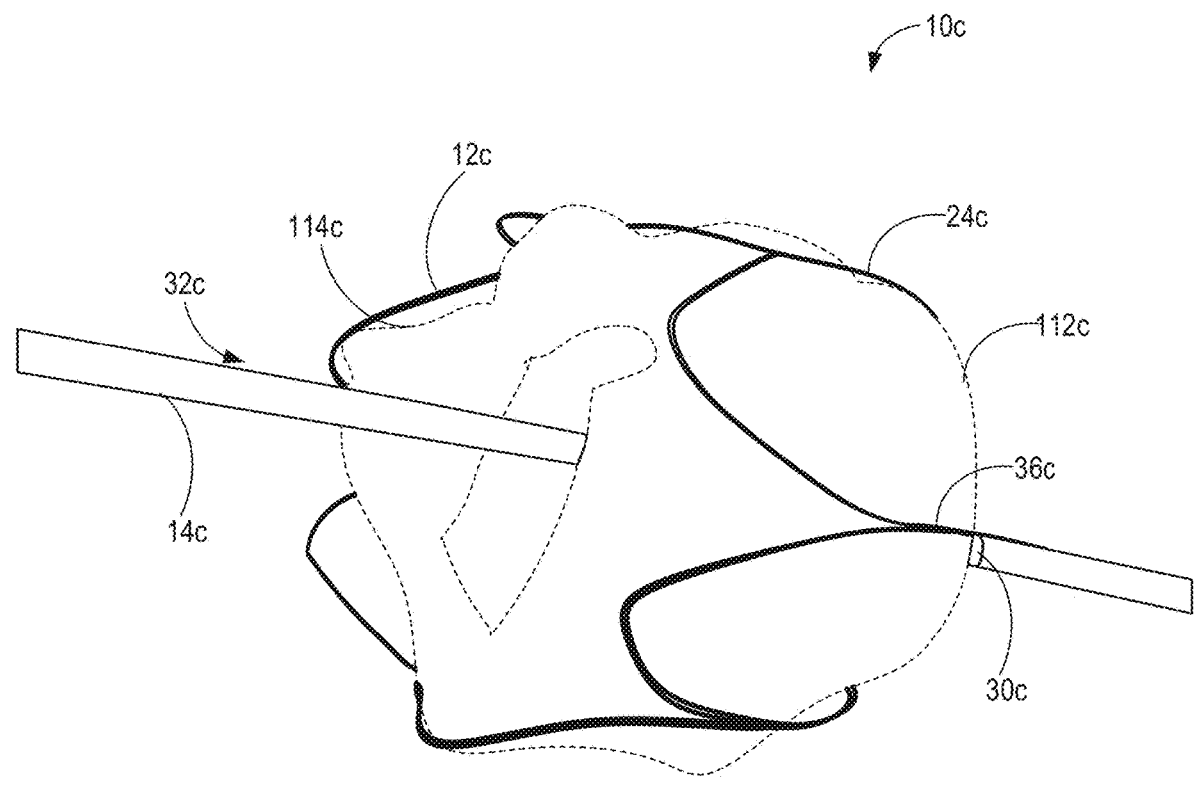
FIG. 6B is a photograph of a proximally directed perspective view of the atrioventricular prosthesis device of FIG. 6A.

With reference to FIGS. 6A and 6B, a frame 12c for use with an atrioventricular prosthesis device 10c is illustrated, according to another aspect of the invention. As in previously described examples, the frame 12c comprises a plurality of elongated members 24c formed from a super-elastic material, such as Nitinol. The members 24c are mounted to a central member 14c at a proximal end 30c thereof. The distal end 32c of the frame 12c is substantially open and is not mounted to the central member 14c. Each elongated member 24c is connected to an adjacent member 24c to form a wire pair, in which adjacent wires are connected together at a connection point 36c between the proximal end 30c and a middle portion 22c of the frame 12. As in previously described examples, each member 24c is attached to a member 24c of an adjacent wire pair to form a plurality of petal-shaped lattices 38c. A valve construct 110c is at least partially enclosed in a central cavity 16c defined by the frame 12c. A support or annular portion 112c of the valve construct 110c is connected to the elongated members 24c. The valve construct 110c also includes leaflets 114c that extend longitudinally and radially inward from the annular portion 112c to form the valve structure. For example, as shown in FIGS. 6A and 6B, the valve construct 110c includes three leaflets 114c and is shaped to correspond to the structure of a tricuspid valve.

Exemplary Valve Construct:

With reference again to FIGS. 1A, 1B, 2, and 3, the valve construct 110 is at least partially enclosed within the circumference of the frame 12, such that the annular portion 112 defines a longitudinal axis and an aperture for blood flow passing through the valve 110. The annular portion 112 is attached to the frame 12 and spaced from the distal end 32 thereof to align with an atrioventricular valve annulus.

Fabrication processes for attaching the valve construct 110 to the frame include, for example and without limitation, either stitching or suturing methods (e.g., as are commonly used for Dacron polyester based endovascular devices) and encapsulation methods using ultra-thin ePTFE membrane materials (e.g., as used for ePTFE based endovascular devices). In another example, the valve construct 110 is attached to the frame 12 by one or more of microscale mechanical clamping, microscale suturing, and/or direct deposition of electrospun leaflet material onto the frame 12. In one preferred example, the valve construct 110 is attached by a process comprising (1) suturing using ultra-thin nitinol or polymer thread (e.g., <100 m thick) and (2) direct deposition of a PEUU electrospun layer on the nitinol frame.

The leaflets 114 are movable relative to the annular portion 112 between an open configuration in which the leaflet(s) 114 permit blood flow through the aperture in a first direction, and a closed configuration in which the leaflet restricts blood flow through the aperture in a second direction opposite the first. The leaflets 114 are joined with adjacent leaflets at a portion of their edges immediately adjacent to the annular portion 112, and are not joined at a portion distal to the annular portion 112, to permit blood to flow through the valve construct 110 when it is open. When the valve construct 110 is closed, the leaflets 114 are concave, meaning that the concavity extends towards a central axis of the aperture of the annular portion 112, and the leaflets 114 contact or coaptate with adjacent leaflets 114 to form a seal. Unless indicated otherwise, in reference to the valve structures described herein, concave means curved or extending towards the rotational, longitudinal, or central axis, and convex, means curved or extending outwards away from the rotational, longitudinal, or central axis.

Figure 7A:
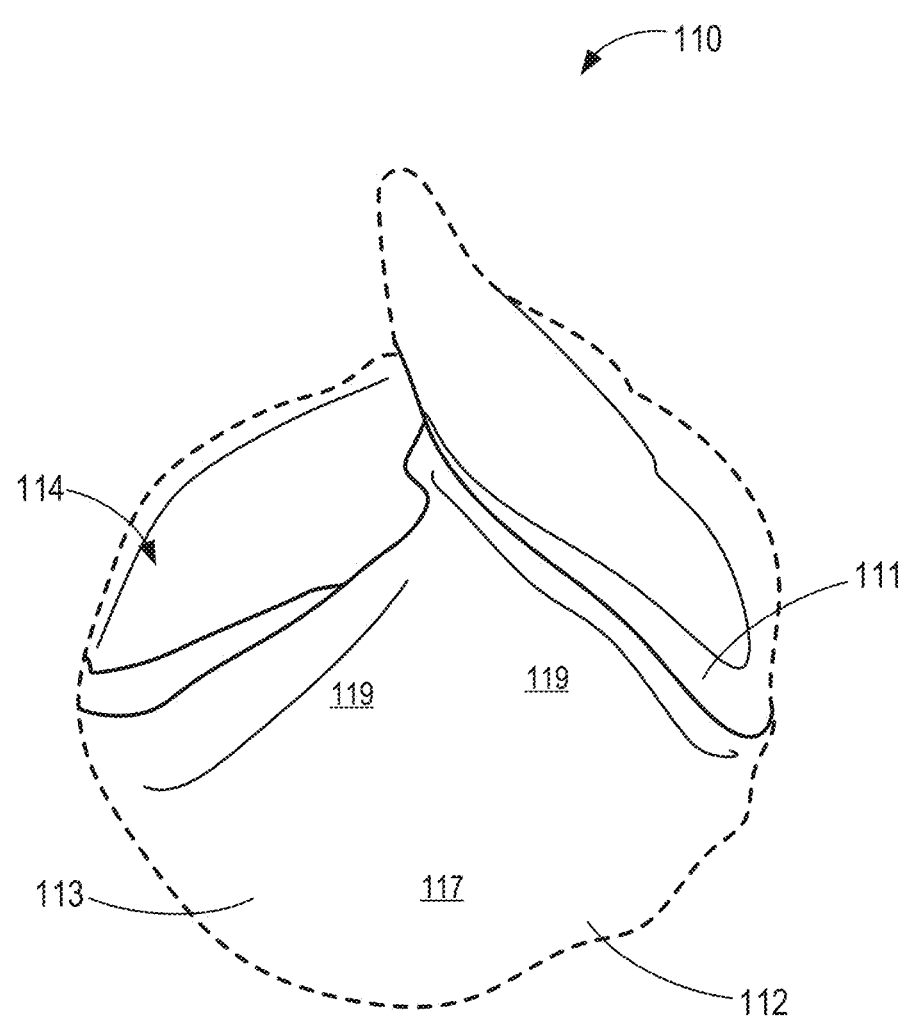
FIG. 7A is a photograph of a valve construct of the atrioventricular prosthesis device, according to an aspect of the invention.
Figure 7B:
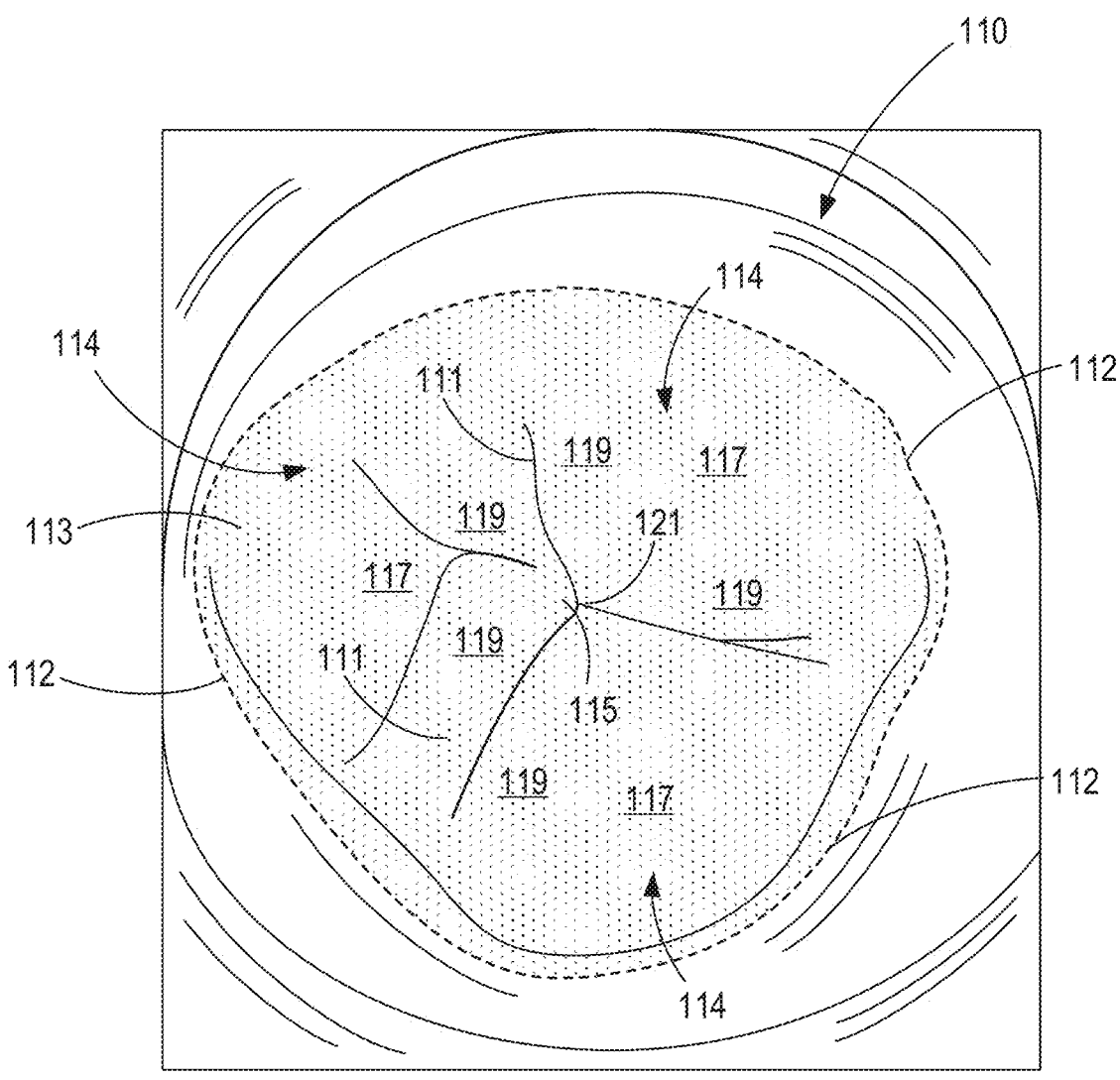
FIG. 7B is another photograph of the valve construct of FIG. 7A.

With reference to FIGS. 7A and 7B, the leaflets 114 are approximately triangular or leaf-shaped structures having a proximal portion 113 extending radially inward and longitudinally from the annular portion 112, a distal tip portion 115, and edges 111 extending therebetween. The leaflets 114 comprise a belly or central region 117 partially enclosed by the edges 111. The central region 117 comprises a longitudinally and/or radially concave surface that extends in an inward direction from the periphery of the leaflet 114. For example, the concave surface can extend longitudinally inward from the proximal portion 113 of the leaflet 114 and radially inward from the edges 111. In some examples, edges 111 of a leaflet 114 near the annular portion 112 are partially connected to edges 111 of an adjacent leaflet 114 to form a commissure region 119 between the adjacent leaflets 114. Some portions of the edges 111 of adjacent leaflets 114 are not connected together, thereby defining a slit or opening (e.g., an aperture 121) of the valve construct 110 and, in relevant part, to permit the valve construct 110 to transition between its open and sealed states. When connected to the frame 12 in the manner discussed herein, the leaflets 114 are concave structures that bulge from the annular portion 112 of the valve construct 110 toward the central member 14 thereof. The structure and material components of the valve construct 110 will now be described in detail.

Polymeric Component:

In some aspects, the valve construct 110 is formed from a biodegradable and biocompatible scaffold material, such as a synthetic polymeric composition. One useful polymeric composition is poly(ester-urethane)urea (PEUU), which can be synthesized using putrescine as a chain extender and the two-step solvent synthesis method described below. PEUU has high elasticity and mechanical strength coupled with controllable biodegradative and cell-adhesive properties. See Guan J, et al., Synthesis, characterization, and cytocompatibility of elastomeric, biodegradable poly(ester-urethane) ureas based on poly(caprolactone) and putrescine, *J Biomed Mater Res*, 2002 Sep. 5; 61(3):493-503. PEUU has been adopted for a number of in vivo scenarios including cardiac patch, abdominal wall repair, or vascular grafts. See Fujimoto K, et al., An Elastic, Biodegradable Cardiac Patch Induces Contractile Smooth Muscle and Improves Cardiac Remodeling and Function in Subacute Myocardial Infarction, *J Am Coll Cardiol*, 2007 Jun. 12; 49(23): 2292-2300; Hashizume R, et al., Morphological and mechanical characteristics of the reconstructed rat abdominal wall following use of a wet-electrospun biodegradable polyurethane elastomer scaffold, *Biomaterials* 31:3253-65 (2010); and Soletti L, et al., A bi-layered elastomeric scaffold for tissue engineering of small-diameter vascular grafts, *Acta Biomaterialia* 6:110-22 (2010). Alternative chemistries allow for polyurethanes having added non-thrombogenic chemical moieties and for use of non-degradable polyurethanes as permanent valvular structures not meant to be remodeled in situ. Additional biodegradable polymeric compositions are known in the art, and exhibit suitable strength and elasticity for use along with, or substituting for PEUU, e.g., as described in further detail below.

In some aspects, the valve construct 110 is produced by electrodeposition and/or electrospinning of PEUU. Optionally, orientation of electrospun fibers in the valve construct 110 is controlled to impart a desired shape and curvature to the leaflet structures. For example, in some aspects, the structure of the leaflet 114 is formed by electrodeposited and/or electrospun fibers oriented predominately, (e.g, >50%, >60%, >70%) in a circumferential direction within the belly or central region 117 thereof. Electrodeposited fibers adjacent to the edges 111 (e.g., in the commissure region 119) of the leaflets 114 and/or in the annular portion 112 of the valve construct 110 are oriented predominantly in an axial direction (e.g., parallel to the longitudinal axis L of the frame 12 (shown in FIG. 1A). In some aspects, the fibers and/or fiber matrix can be anisotropic in both the central region 117 and the commissure region 119, but with the fiber orientation at the central region 117 being more circumferential than at the commissure region 119.

Extracellular Matrix Component:

In some aspects, the valve construct 110 further comprises a biodegradable, biomacromolecular component, such as an extracellular matrix (ECM)-derived material, for example, decellularized tissue. Optionally, the ECM-derived material is provided in the form of a sheet or gel. Optionally, the valvular structure is made wholly from ECM materials, such as sheets of ECM materials prepared, for example, from bovine pericardium or porcine leaflet.

In one aspect, the valve construct 110 is formed from a polymeric composition comprising a combination of the synthetic polymer and an ECM gel, as is described, for example, in PCT Publication No. WO 2012/024390 entitled "Biohybrid composite scaffold". Notably, the ECM gel component, while useful in promoting cell growth (including, but not limited to, one or more of colonization, propagation, infiltration, cell viability, differentiation, tissue repair), may not have sufficient strength for use as a tissue repair scaffold in a patient. Optionally, a ratio of polymer to ECM is selected to display excellent cellular infiltration and adequate tensile strength and elasticity. An exemplary ratio of polymer to ECM is >50%:<50%, and preferably within a range of 70%-85%:15%-30%. In some aspects, a material having the desired ratio is obtained by co-depositing the biodegradable, elastomeric polymer and the ECM gel by e.g., electrospinning. For example, the synthetic biodegradable, elastomeric polymer is electrospun and the ECM gel is sprayed, e.g. electrosprayed.

In its broadest sense, to produce an ECM gel according to one non-limiting example, ECM-derived scaffold materials, e.g., decellularized or devitalized tissue, are communited and solubilized to form a hydrogel. In one example, the solubilized hydrogel is not dialyzed. Solubilization may be achieved by digestion with a suitable protease, such as the endoproteases trypsin, chymotrypsin, pepsin, papain and elastase. In certain non-limiting examples, the method for making such a gel comprises: (i) comminuting an extracellular matrix, (ii) solubilizing intact, non-dialyzed and/or non-cross-linked extracellular matrix by digestion with an acid protease in an acidic solution, e.g., at a pH of approximately 2.0 (e.g. 0.01N HCl), to produce a digest solution, (iii) raising the pH of the digest solution to a pH between 7.2 and 7.8 to produce a neutralized digest solution, and (iv) gelling the solution at a temperature greater than approximately 25° C.

"ECM material" is a material prepared from an extracellular matrix-containing tissue, and includes decellularized or devitalized tissue. ECM material can be used to produce gels according to the methods, compositions and devices as described herein (see generally, U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666).

In certain examples, ECM material is decellularized tissue prepared from tissue of a vertebrate animal, for example and without limitation, from a mammal, including, but not limited to, human, monkey, pig, cow and sheep. The ECM material can be prepared from any organ or tissue, including without limitation, urinary bladder, intestine, liver, esophagus and dermis. In one example, the ECM material is decellularized tissue isolated from urinary bladder tissue. The ECM material may or may not include the basement membrane portion of the tissue. In certain examples, the ECM material includes at least a portion of the basement membrane. In certain examples, the ECM material is prepared from pericardium or valve leaflets obtained, for example from a pig, cow, horse, monkey, or human, for example bovine pericardium or porcine valve leaflets.

As an example, decellularized tissue is isolated from harvested porcine urinary bladder to prepare urinary bladder matrix (UBM). Excess connective tissue and residual urine are removed from the urinary bladder. The tunica serosa, tunica muscularis externa, tunica submucosa and most of the muscularis mucosa can be removed by mechanical abrasion or by a combination of enzymatic treatment, hydration, and abrasion. Mechanical removal of these tissues can be accomplished by abrasion using a longitudinal wiping motion to remove the outer layers (particularly the abluminal smooth muscle layers) and even the luminal portions of the tunica mucosa (epithelial layers). Mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze. The epithelial cells of the tunica mucosa can also be dissociated by soaking the tissue in a de-epithelializing solution, for example and without limitation, hypertonic saline. The resulting UBM comprises basement membrane of the tunica mucosa and the adjacent tunica propria.

In another example, the epithelial cells are delaminated first by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion.

In one example, the decellularized tissue is prepared by abrading porcine bladder tissue to remove the outer layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. Care is taken to prevent perforation of the submucosa. After these tissues are removed, the resulting ECM material consists mainly of the tunica submucosa.

ECM material is decellularized, sterilized and/or dried by any useful method. The ECM material can be sterilized by any of a number of standard methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. The material can also be sterilized by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. More typically, ECM is disinfected by immersion in 0.1% (v/v) peracetic acid (a), 4% (v/v) ethanol, and 96% (v/v)

sterile water for 2 h. The decellularized tissue is then washed twice for 15 min with PBS (pH=7.4) and twice for 15 min with deionized water.

Commercially available ECM materials derived from small intestinal submucosa or SIS include, but are not limited to, Surgisis™, Surgisis-ES™, Stratasis™, and Stratasis-ES™ (Cook Urological Inc.; Indianapolis, Indiana) and GraftPatch™ (Organogenesis Inc.; Canton Massachusetts). In another example, the ECM material is derived from dermis. Commercially available preparations include, but are not limited to Pelvicol™ (crosslinked porcine dermal collagen, sold as Permacol™ in Europe; Bard Medical Division, Covington, GA), Repliform™ (Microvasive; Boston, Massachusetts) and Alloderm™ (LifeCell; Branchburg, New Jersey). In another example, the ECM is derived from urinary bladder. Commercially available preparations include, but are not limited to UBM (Acell Corporation; Jessup, Maryland).

In one non-limiting example, the decellularized tissue is lyophilized, comminuted, and is then solubilized with an acid protease. In certain aspects, the decellularized tissue is not dialyzed and/or is not crosslinked (subjected to a cross-linking method) prior to digestion with the acid protease. The acid protease may be, without limitation, pepsin or trypsin, and in one example is pepsin. The decellularized tissue typically is solubilized at an acid pH suitable or optimal for the protease, between pH 1.5 and 3, for example in a 0.01M HCl solution (pH~2). The solution typically is solubilized for 12-48 hours, depending upon the tissue type, with mixing (stirring, agitation, admixing, blending, rotating, tilting, etc.). Once the decellularized tissue is solubilized the pH is raised to between 7.2 and 7.8, and according to one example, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. The neutralized digest solution is gelled at temperatures approaching 37° C., typically at any temperature over 25° C., though gelation proceeds much more rapidly at temperatures over 30° C. and as the temperature approaches physiological temperature (37° C.). The method typically does not include a dialysis step prior to gelation, yielding a more-complete ECM-like matrix that typically gels at 37° C. more slowly than comparable collagen or dialyzed ECM preparations.

The ECM gel can be sprayed, for example, as a liquid or hydrogel and may be combined with other polymers, as described herein. An ECM gel is reverse-gelling, meaning it forms a hydrogel when its temperature is raised and may have an LCST (Lower Critical Solution Temperature) above or below the temperature at which the solution is sprayed, and as such will have a gel transition at a temperature higher, equal to or lower than the temperature at which the ECM gel is sprayed. For example, if the hydrogel is sprayed at room temperature (that is approximately 20-25° C.) or less and the LCST of the ECM material is greater than the spraying temperature, but, e.g., less than 37° C., the material can be sprayed and will later gel on warming. See, e.g. United States Patent Publication No. 20080260831, incorporated herein by reference for its technical disclosure. See also, Stankus et al., Hybrid nanofibrous scaffolds from electro-spinning of a synthetic biodegradable elastomer and urinary bladder matrix, J Biomater. Sci. Polym. Ed. (2008) 19(5):

635-652. In the Stankus article, PEUU was mixed with solubilized UBM ECM and was electrospun.

Exemplary Polymer Compositions:

As discussed above, the annular portion 112 and/or leaflets 114 of the valve construct are formed, for example, from one or more polymeric compositions or polymer materials. As used herein, the term "polymer" refers to both synthetic polymeric components and biological polymeric components. "Biological polymer(s)" are polymers that are obtained from biological sources, such as, without limitation, mammalian or vertebrate tissue, as in the case of certain ECM-derived compositions. Biological polymers can be modified by additional processing steps. Polymer(s), in general include, without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s). Polymer(s) are formed into any useful form such as, without limitation, a hydrogel, a porous mesh, a fiber, woven mesh, or non-woven mesh, such as, for example and without limitation, a non-woven mesh formed by electrospinning.

In some aspects, the valve construct 110 is formed from a porous deposited biodegradable, elastomeric polymer. As used herein, the term "porosity" refers to a ratio between a volume of all the pores within the polymer composition and a volume of the whole polymer composition. For instance, a polymer composition with a porosity of 85% would have 85% of its volume containing pores and 15% of its volume containing the polymer. In certain non-limiting embodiments, the porosity of the structure is at least 60%, 65%, 70%, 75%, 80%, 85%, or 90%, or increments therebetween. In another non-limiting example, an average pore size of the structure is between 0.1 and 300 microns, preferably between 0.1 and 100 microns, and more preferably between 1-25 microns, including increments therebetween. For example and without limitation, a structure that acts as a barrier to bacteria and other pathogens may have an average pore size of less than 0.5 microns or less than 0.2 microns. In one example, the structures described herein are manufactured by electrospinning. It therefore is often advantageous to adjust the pore size or degree of porosity by varying the polymer concentration of the electrospinning solution or by varying the spinning distance from the nozzle to the target. For example and without limitation, the average pore size may be increased by increasing the amount of polymeric components within the suspension used for electrospinning, which results in larger fiber diameters and therefore larger pore sizes. In another non-limiting example, the average pore size can be increased by increasing spinning distance from the nozzle to the target, which results in less adherence between fibers and a looser matrix. Where ECM gel is co-deposited during the electrospinning, many of the pores (that is a large percentage of the pores or interstices) in the deposited polymer are filled with the ECM gel.

Generally, the polymeric compositions suitable for the structures described herein are any polymer that is biocompatible and can be biodegradable. In certain non-limiting examples, the biodegradable polymers comprises homopolymers, copolymers, and/or polymeric blends comprising, without limitation, one or more of the following monomers: glycolide, lactide, caprolactone, dioxanone, and trimethylene carbonate. In other non-limiting examples, the polymer(s) comprise labile chemical moieties, non-limiting examples of which include esters, anhydrides, polyanhydrides, or amides, which can be useful in, for example and without limitation, controlling the degradation rate of the scaffold and/or the release rate of therapeutic agents from the scaffold. Alternatively, the polymer(s) may contain polypeptides or biomacromolecules as building blocks which are susceptible to chemical reactions once placed in situ. In one non-limiting example, the polymer composition comprises a polypeptide comprising the amino acid sequence alanine-alanine-lysine, which confers enzymatic lability to the polymer. In another non-limiting examples, the polymer composition comprises a biomacromolecular component derived from an ECM. For example, as described in further detail below, the polymer composition may comprise the biomacromolecule collagen so that collagenase, which is present in situ, can degrade the collagen. The polymers used herein may be elastomeric, meaning they change shape on application of a deforming force and substantially return to an original shape when the deforming force is removed.

In another non-limiting example, the synthetic polymeric component comprises any hydrolytically, chemically, biochemically, and/or proteolytically labile group, non-limiting examples of which include an ester moiety, amide moiety, anhydride moiety, specific peptide sequences, and generic peptide sequences.

A number of biocompatible, biodegradable elastomeric (co)polymers are known and have been established as useful in preparing cell growth matrices, including biodegradable poly(ester urethane) urea (PEUU), poly(ether ester urethane) urea (PEEUU), poly(ester carbonate)urethane urea (PECUU) and poly(carbonate)urethane urea (PCUU). In general, useful (co)polymers comprise monomers derived from alpha-hydroxy acids including polylactide, poly(lactide-co-glycolide), poly(L-lactide-co-caprolactone), polyglycolic acid, poly(dl-lactide-co-glycolide), poly(l-lactide-co-dl-lactide); monomers derived from esters including polyhydroxybutyrate, polyhydroxyvalerate, polydioxanone and polygalactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

The biodegradable polymers are, for example and without limitation, homopolymers, copolymers, and/or polymeric blends. In certain examples, the polymer(s) comprise, without limitation, one or more of the following monomers: glycolide, lactide, caprolactone, dioxanone, and trimethylene carbonate. According to certain examples, the polymer is chosen from one or more of: a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(l-lactide-co-dl-lactide), a polymer comprising a lactone monomer, a polycaprolactone, polymer comprising carbonate linkages, a polycarbonate, a polyglyconate, a poly(trimethylene carbonate), a poly(glycolide-co-trimethylene carbonate), a poly (glycolide-co-trimethylene carbonate-co-dioxanone), a polymer comprising urethane linkages, a polyurethane, a poly(ester urethane) urea, a poly(ester urethane) urea elastomer, a poly(ester carbonate urethane) urea, a poly(carbonate urethane) urea, a polycarbonate urethane, a polyester urethane, a polymer comprising ester linkages, a polyalkanoate, a polyhydroxybutyrate, a polyhydroxyvalerate, a polydioxanone, a polygalactin, a natural polymer, chitosan, collagen, elastin, alginate, cellulose, hyaluronic acid and gelatin. In one example, the polymer composition comprises a poly(ester urethane) urea with from about 25% wt. to about 75% wt. collagen. In another example, the polymer composition comprises elastin, collagen or a mixture thereof, for example and without limitation from about 25% wt. to about 75% wt. of a mixture of collagen and elastin, which are in approximately (about) equal amounts. In yet another example, the polymer comprises a polycaprolactone. In yet another example, the polymer comprises a polycaprolactone diol. In yet another example, the polymer comprises a triblock copolymer comprising polycaprolactone, poly(ethylene glycol), and polycaprolactone blocks The polymer composition further comprises, for example and without limitation, a biomacromolecular component derived from ECM. In one examples, the polymer composition comprises the biomacromolecule collagen so that collagenase, which is present in situ, can degrade the collagen. As an example, the polymer composition may comprise one or both of a collagen and an elastin. Collagen is a common ECM component, and typically is degraded in vivo at a rate faster than many synthetic bioerodable polymers. Therefore, manipulation of collagen content in the polymer composition may be used as a method of modifying bioerosion rates in vivo. Collagen may be present in the polymer composition in any useful range, including, without limitation, from about 2% wt. to about 95% wt., preferably in a range of from about 25% wt. to about 75% wt., inclusive of all ranges and points therebetween, including from about 40% wt. to about 75% wt., including about 75% wt. and about 42.3% wt. Elastin may be incorporated into the polymer composition in order to provide increased elasticity. Elastin may be present in the polymer composition in any useful range, including without limitation, from about 2% wt. to about 50% wt., inclusive of all ranges and points therebetween, including from about 40% wt. and about 42.3% wt., inclusive of all integers and all points therebetween and equivalents thereof. In one non-limiting example, collagen and elastin are present in approximately equal amounts in the polymer composition. In another embodiment, the sum of the collagen and elastin content in the polymer composition is in any useful range, including, without limitation, from about 2% wt. to about 95% wt., and preferably in the range of from about 25% wt. to about 75% wt., inclusive of all ranges and points therebetween, including from about 40% wt. to about 75% wt., including about 75% wt. and about 42.3% wt.

The monomer feed ratio and hence the monomer residue composition of any copolymer compositions as described herein can be varied so long as the resultant copolymer can be used to manufacture a valve construct as described herein. Variations in the monomer residue composition of copolymer compositions described herein can be readily accomplished and evaluated by one of ordinary skill in the art for usefulness in a heart valve construct.

As discussed above, in some non-limiting examples, the polymer composition comprises a biodegradable poly(ester urethane) urea elastomer (PEUU). PEUU can be manufactured by reacting a diol with a diisocyanate to form a prepolymer and then reacting the prepolymer with a diamine. A non-limiting example of such a PEUU is an elastomeric polymer made from polycaprolactone diol ($M_W$ 2000) and 1,4-diisocyanatobutane, using a diamine chain extender such as putrescine. One non-limiting example or method for preparing a PEUU polymer is a two-step polymerization process whereby polycaprolactone diol ($M_W$ 2000), 1,4-diisocyanatobutane, and diamine are combined in a 2:1:1 molar ratio. In the first step to form the pre-polymer, a 15 wt % solution of 1,4-diisocyanatobutane in DMSO (dimethyl sulfoxide) is stirred continuously with a 25% wt solution of polycaprolactone diol in DMSO. Then, stannous octoate is added and the mixture is allowed to react at 75° C. for 3 hours. In the second step, the pre-polymer is reacted with a diamine to extend the chain and to form the polymer. In one example, the diamine is putrescine, which is added drop-wise while stirring and allowed to react at room temperature for 18 hours. In one example, the diamine is lysine ethyl ester, which is dissolved in DMSO with triethylamine, added to the prepolymer solution, and allowed to react at 75° C. for 18 hours. After the two step polymerization process, the polymer solution is precipitated in distilled water. Then, the wet polymer is immersed in isopropanol for three days to remove any unreacted monomers. Finally, the polymer is dried under vacuum at 50° C. for 24 hours.

In another non-limiting example, the polymer composition comprises poly(ether ester urethane) urea elastomer (PEEUU). For example and without limitation, PEEUU may be made by reacting polycaprolactone-b-polyethylene glycol-b-polycaprolactone triblock copolymers with 1,4-diisocyanatobutane and putrescine. In one non-limiting example, PEEUU is obtained by a two-step reaction using a 2:1:1 reactant stoichiometry of 1,4-diisocyanatobutane:triblock copolymer:putrescine. According to one non-limiting example, the triblock polymer can be prepared by reacting poly(ethylene glycol) and s-caprolactone with stannous octoate at 120° C. for 24 hours under a nitrogen environment. The triblock copolymer is then washed with ethyl ether and hexane, and dried in a vacuum oven at 50° C. In the first step to form the pre-polymer, a 15% wt solution of 1,4-diisocyanatobutane in DMSO is stirred continuously with a 25% wt solution of triblock copolymer in DMSO. Then, stannous octoate is added and the mixture is allowed to react at 75° C. for 3 hours. In a second step, putrescine is added drop-wise under stirring to the prepolymer solution and allowed to react at room temperature for 18 hours. The PEEUU polymer solution is then precipitated with distilled water. The wet polymer is immersed in isopropanol for 3 days to remove unreacted monomer and dried under vacuum at 50° C. for 24 hours.

In another non-limiting example, the polymer composition comprises a poly(ester carbonate)urethane urea (PECUU) or a poly(carbonate)urethane urea (PCUU), which are described, for example, in Hong et al., Tailoring the degradation kinetics of poly(ester carbonate urethane)urea thermoplastic elastomers for tissue engineering scaffolds, Biomaterials 31 (2010) 4249-4258). Poly(ester carbonate urethane)urea (PECUU) is synthesized, for example using a blended soft segment of polycaprolactone (PCL) and poly (1,6-hexamethylene carbonate) (PHC) and a hard segment of 1,4-diisocyanatobutane (BDI) with chain extension by putrescine. Different molar ratios of PCL and PHC can be used to achieve different physical characteristics. Putrescine is used as a chain extender by a two-step solvent synthesis method. In one example, the (PCL+PHC):BDI:putrescine molar ratio is defined as 1:2:1. Variable molar ratios of PCL and PHC (e.g., PCL/PHC ratios of 100/0 (yielding a PEUU), 75/25, 50/50, 25/75 and 0/100 (yielding a PCUU)) are completely dissolved in DMSO in a 3-neck flask with argon protection and then BDI is added to the solution, following 4 drops of Sn(Oct)$_2$. The flask is placed in an oil bath at 70° C. After 3 h, the pre-polymer solution is cooled at room temperature and then a putrescine/DMSO solution is added dropwise into the agitated solution. The final polymer solution concentration is controlled to be approximately 4% (w/v). The flask is then placed in an oil bath and kept at 70° C. overnight. The polymer is precipitated in an excess volume of cool deionized water and then dried in a vacuum at 60° C. for 3 days. The polyurethane ureas synthesized from the different PCL/PHC molar ratios defined above are referred to as PEUU, PECUU 75/25, PECUU 50/50, PECUU 25/75 and PCUU, respectively. In practice, the yields of all final products using this method is approximately 95%.

Diamines and diols are useful building blocks for preparing the (co)polymer compositions described herein. Diamines as described above have the structure H$_2$N—R—NH$_2$ where "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as poly-caprolactone-PEG copolymers, including polycaprolactone-b-polyethylene glycol-b-polycaprolactone triblock copolymers of varying sizes. Other building blocks for useful diols include, without limitation glycolides (e.g. polyglycolic acid (PGA)), lactides, dioxanones, and trimethylene carbonates. Diisocyanates have the general structure OCN—R—NCO, where "R" is an aliphatic or aromatic hydrocarbon or a hydrocarbon comprising aromatic and aliphatic regions. The hydrocarbon may be linear or branched.

In additional aspects, the polymer composition comprises polyethylene terephthalate (PET, e.g., DACRON). Of note, PET is less biodegradable than the copolymers described above, and is stiffer. PET scaffolds structures are made essentially in the manner described herein for PEUU and other polymer compositions described herein. Polymer concentrations and infusion rates may be altered to accommodate the different qualities of the PET composition, for example and without limitation, for PET, 20% w/v in HFIP at 12 mL/h infusion rate, as used in the examples below.

In other examples, the polymer composition comprises a tyrosine polyarylate (TPA). As with PET, TPA is less biodegradable than the polyurethane copolymers described above, and also is stiffer. TPA scaffolds structures are made essentially in the manned described herein for PEUU and other polymer compositions. Polymer concentrations and infusion rates may be altered to accommodate the different qualities of the TPA composition, for example and without limitation, for TPA, 12% w/v in HFIP at 20 mL/h infusion rate. Tyrosine polyarylates are commonly prepared from an aliphatic acid and a tyrosine-derived diphenol. Non-limiting examples of useful aliphatic acids include: succinic acid, adipic acid, sebacic acid, and dicarboxylic acid chlorides or anhydrides. Non-limiting examples of tyrosine-derived diphenols include desaminotyrosyl-tyrosine alkyl esters, where the alkyl is, for example, one of ethyl, hexyl and octyl) (DTE). As an example, Poly(DTE-co-27.5 DT succinate) is used. TPAs and methods of making TPAs are described, for example, in U.S. Pat. No. 5,216,115 and U.S. Patent Application Publication No. 2011/0082545, each of which is incorporated herein by reference for its technical disclosure. Additional references disclosing TPA compositions and methods of making and using those compositions include: Fiordeliso, J, et al., Design, synthesis, and preliminary characterization of tyrosine-containing polyarylates: new biomaterials for medical applications, *J Biomater Sci Polym Ed.*, 1994; 5(6):497-510; Huang, X, et al., A library of L-tyrosine-derived biodegradable polyarylates for potential biomaterial applications, part I: synthesis, characterization and accelerated hydrolytic degradation, *J Biomater Sci Polym Ed.*, 2009; 20 (7-8):935-55; and Bourke, S L, et al., Polymers derived from the amino acid L-tyrosine: polycarbonates, polyarylates and copolymers with poly(ethylene glycol), *Adv Drug Deliv Rev.* 2003 Apr. 25; 55(4):447-66.

Therapeutic Agents:

In some aspects, the device 10 further comprises therapeutic agents that are, for example and without limitation, released to the patient as the structures degrade within the patient's body. In some examples, individual building blocks of the polymeric compositions that form the portions of the valve construct 110 are selected such that the building blocks themselves provide a therapeutic benefit when released in situ through the degradation process. In one example, one of the polymer building blocks is putrescine, which has been implicated as a substance that causes cell growth and cell differentiation.

In another example, at least one therapeutic agent is added to the scaffold or composition described herein before it is implanted in the patient or otherwise administered to the patient. Generally, the therapeutic agents include substances that are coated on, embedded into, absorbed into, adsorbed to, or otherwise attached to or incorporated onto or into the structure and/or incorporated into a drug product that would provide a therapeutic benefit to a patient. Non-limiting examples of such therapeutic agents include, without limitation, antimicrobial agents, growth factors, emollients, retinoids, and topical steroids. Each therapeutic agent may be used alone or in combination with other therapeutic agents. For example and without limitation, a structure comprising neurotrophic agents or cells that express neurotrophic agents may be applied to a wound that is near a critical region of the central nervous system, such as the spine. Alternatively, the therapeutic agent may be blended with the polymer while a polymer is being processed. For example, the therapeutic agent may be dissolved in a solvent (e.g., DMSO) and added to the polymer blend during processing. In another example, the therapeutic agent is mixed with a carrier polymer (e.g., polylactic-glycolic acid microparticles) which is subsequently processed with an elastomeric polymer. By blending the therapeutic agent with a carrier polymer or elastomeric polymer itself, the rate of release of the therapeutic agent may be controlled by the rate of polymer degradation.

In certain aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), Human Vascular Endothelial Growth Factor-165 (hVEGF$_{165}$), Vascular endothelial growth factor A (VEGF-A), Vascular endothelial growth factor B (VEGF-B), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minnesota; Biovision, Inc, Mountain View, California; ProSpec-Tany TechnoGene Ltd., Rehovot, Israel; and Cell Sciences®, Canton, Massachusetts.

In certain aspects, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain aspects, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin; nitro-fatty acids, such as nitro-oleic acid or nitro-conjugated linoleic acid. Other drugs that may promote wound healing and/or tissue regeneration may also be included.

Figure 8:
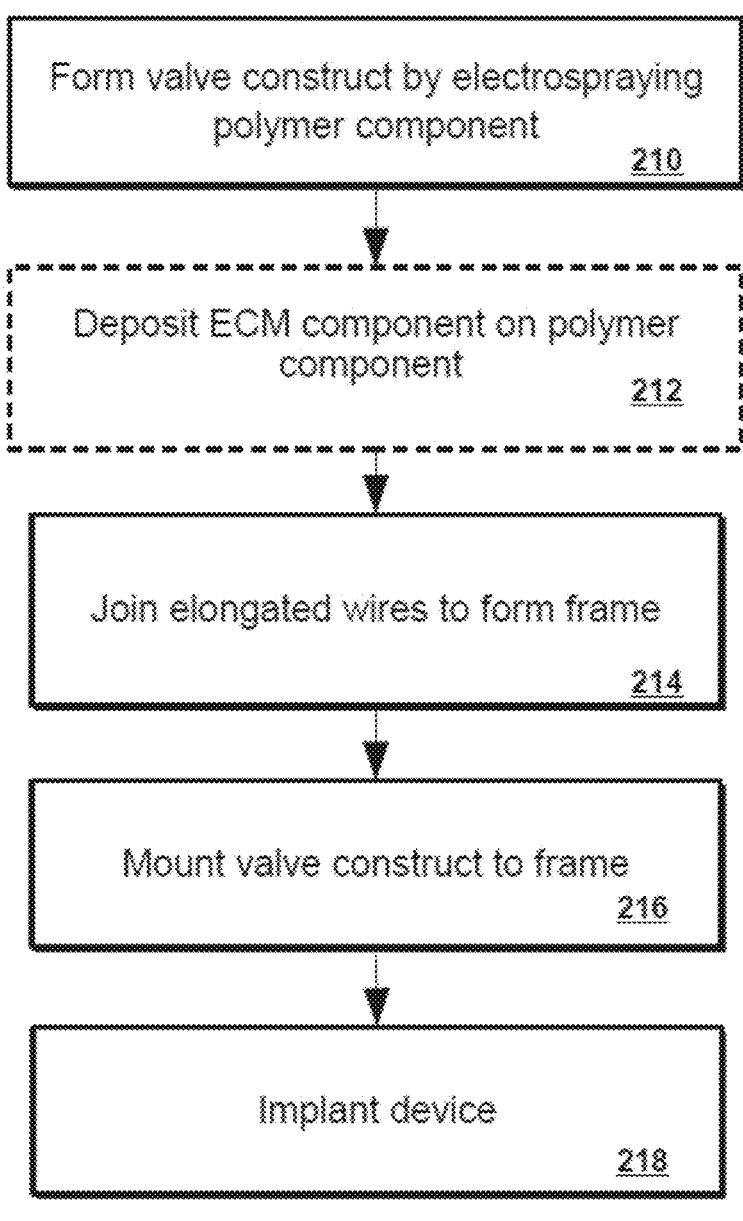
FIG. 8 is a flow chart of steps for manufacture of an atrioventricular prosthesis device according to an aspect of the invention.

Manufacturing Methods:

With reference to FIG. 8, a method for forming the atrioventricular prosthesis device disclosed herein will now be discussed in detail.

As shown in box 210, in one non-limiting example, a valve construct is provided by first forming a polymeric material by electrospinning. In one example, the polymer component of the valve construct is made by electrospinning of a biodegradable, elastomeric polymer. Optionally, as shown at box 212, an ECM gel, a blood product, cell culture medium, water, PBS, saline, or other liquid, is deposited on the polymer component by spraying (e.g., electrospraying). Optionally, the electrospinning and electrospraying processes are be performed concurrently. Other compounds or components may be incorporated into a structure as described herein by any method, including absorption, adsorption, and/or mixing.

In some examples, electrospinning is used to deposit the biodegradable, elastomeric polymer and, optionally, the ECM gel and/or other liquid, such as a mammalian blood product, media buffer solution, and/or medium. In its simplest sense, electrospinning is caused by the deposit of a liquid composition, such as polymer fibers onto a target surface caused by an electric potential. Electrospinning methods are well-known in the field of tissue engineering and are generally conducted in the following manner. Electrospinning permits fabrication of structures that resemble the scale and fibrous nature of the native ECM. The ECM is composed of fibers, pores, and other surface features at the sub-micron and nanometer size scale. Such features directly impact cellular interactions with synthetic materials such as migration and orientation. Electrospinning also permits fabrication of oriented fibers to result in structures with inherent anisotropy. These aligned structures influence cellular growth, morphology and ECM production. For example, Xu et al. identified smooth muscle cell (SMC) alignment with poly(L-lactide-co-F-caprolactone) fibers. See Xu C Y, et al., Aligned biodegradable nanofibrous structure: a potential for blood vessel engineering, *Biomaterials* 2004 (25) 877-86. Lee et al. submitted aligned non-biodegradable polyurethane to mechanical stimulation and found cells cultured on aligned scaffolds produced more ECM than those on randomly organized scaffolds. See Lee C H, et al., Nanofiber alignment and direction of mechanical strain affect the ECM production of human ACL fibroblast, *Biomaterials* 2005 (26) 1261-1270.

In some aspects, the process of electrospinning involves placing a polymer-containing fluid (for example, a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a target (typically a collector screen or rotating mandrel). During electrospinning, the polymer-containing fluid is charged by the application of high voltage to the solution or orifice (for example, about 3-15 kV) and then forced through the small orifice by the metering pump that provides steady flow. While the polymer-containing fluid at the orifice normally would have a hemispherical shape due to surface tension, the application of the high voltage causes the otherwise hemispherically-shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. Optionally, a focusing ring with an applied bias (for example, 1-10 kV) can be used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a non-woven, porous mesh is formed on the biased target. Under certain conditions, for instance with solutions lacking sufficient viscosity and/or electrospun with certain tolerances, a fiber is not formed, but a spray is formed, depositing discrete droplets onto the target instead of a fiber. This is electrospraying.

The properties of the electrospun structures, e.g., elastomeric scaffolds, can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain non-limiting examples, the biased target is moved back and forth in a regular, periodic fashion, such that fibers of the non-woven mesh are substantially parallel to each other. When this is the case, the resulting non-woven mesh may have a higher resistance to strain in the direction parallel to the fibers, compared to the direction perpendicular to the fibers. In other non-limiting examples, the biased target is moved randomly relative to the orifice, so that the resistance to strain in the plane of the non-woven mesh is isotropic. The target can also be electrospun on a rotating mandrel. In this case, the properties of the non-woven mesh may be changed by varying the speed of rotation. The properties of the electrospun structure may also be varied by changing the magnitude of the voltages applied to the electrospinning system. In one non-limiting example, the electrospinning apparatus includes an orifice biased to 12 kV, a target biased to −7 kV, and a focusing ring biased to 3 kV. Moreover, a useful orifice diameter is 0.047" (ID.) and a useful target distance is about 23 cm. Other electrospinning conditions that can be varied include, for example and without limitation, the feed rate of the polymer solutions, the solution concentrations, the polymer molecular weight, the injectors—mandrel gap distance, as well as the injectors—mandrel relative trajectories via CNN control systems.

In further detail and with regard to rotating mandrels, an anisotropic matrix, that is a matrix or article in which at least a portion of which is anisotropic, is prepared by electrospinning on a mandrel, by biasing fiber deposition away from a random, isotropic orientation, resulting in a non-random bias of fiber orientation in a specific orientation, for example with a circumferential bias (at least a portion of deposited fibers are non-randomly oriented in a circumferential direction, resulting in anisotropy), or a longitudinal bias (at least a portion of deposited fibers are non-randomly oriented in a longitudinal direction, resulting in anisotropy). Fiber bias can be introduced in an electrodeposited article by relative movement of the target and the polymer source (e.g., reservoir orifice, needle, pipette tip, etc.). For example, a mandrel target can be rotated at different speeds to generate different degrees of circumferential bias. The mandrel target and/or polymer sources, can be moved, e.g., reciprocated, in a longitudinal direction at different speeds (cycles) and amplitudes while electrospinning to produce varying degrees of longitudinal bias. For example, as shown in FIG. 10B, for the system depicted, a rotational velocity of 1.5 m/s generates an anisotropy ratio (AR, a commonop metric for mechanical anisotropy defined as the ratio between the mechanical strain of the most compliant axis divided by the mechanical strain of the stiffer axis) that matches native anisotropy. Rotational speed of the mandrel, and longitudinal movement of the mandrel and/or polymer source can readily be controlled by computer by a person of ordinary skill in the art.

One measure of fiber orientation is referred to as a fiber orientation index. Orientation index is defined in D'Amore et al., "Characterization of the complete fiber network topology of planar fibrous tissues and scaffolds" *Biomaterials* 31 (20), 5345-5354 (2010). Orientation index can be obtained from the average over all fiber segments of $\cos^2(\theta)$ (COS OI), where $\theta$ represents the angle between a fiber segment and the direction of supposed alignment. The anisotropic portions of the matrices described herein have an orientation index ranging from 0.5 to 0.8

In certain examples, electrospinning is performed using two or more nozzles, wherein each nozzle is a source of a different polymer solution. The nozzles may be biased with different biases or the same bias in order to tailor the physical and chemical properties of the resulting non-woven polymeric mesh. Additionally, many different targets may be used. In addition to a flat, plate-like target, use of a mandrel or a revolving disk as a target is contemplated.

When the electrospinning is to be performed using a polymer suspension, the concentration of the polymeric component in the suspension can also be varied to modify the physical properties of the elastomeric scaffold. For example, when the polymeric component is present at relatively low concentration, the resulting fibers of the electrospun non-woven mesh have a smaller diameter than when the polymeric component is present at relatively high concentration. Without wishing to be limited by theory, it is believed that lower concentration solutions have a lower viscosity, leading to faster flow through the orifice to produce thinner fibers. One skilled in the art can adjust polymer concentrations to obtain fibers of desired characteristics. Useful ranges of concentrations for the polymer component are from 1 wt % to 25 wt %, 4 wt % to 20 wt %, and from 10 wt % to 15 wt %, including increments therebetween for all ranges.

In one non-limiting example, the structure is produced by co-electrospinning a polymer suspension comprising a synthetic polymeric component and a biological polymeric component, along with electrospraying the ECM gel and/or other liquid. In another non-limiting example, the polymeric component of the structure is produced by electrospinning a polymer suspension comprising a synthetic polymeric component from one nozzle and a polymer suspension comprising a biological polymeric component from another nozzle. Non-limiting examples of useful range of high-voltage to be applied to the polymer suspension is from 0.5 to 30 kV, from 5 to 25 kV, and from 10 to 15 kV.

If present, an ECM gel component of the structure is sprayed (e.g. pressure sprayed) or electrosprayed concurrently with the electrospinning of the polymer(s). Likewise, the liquid component of the wet-electrospun layer(s) is sprayed or electrosprayed concurrently with the polymeric constituents.

With continued reference to FIG. 8, as shown at box 214, a frame formed from a flexible, shape memory material is constructed to house the valve construct. In some examples, materials, such as glue, suturing materials, other metallic wires, and welding (or soldering) materials, are used for connecting frame elements together. In other examples, the frame is formed by mechanical bending of straight wires. In other examples, portions of the frame are connected together by micro-laser welding processes to form various lattice structures and patterns. Further, in some examples, various thermal processes including annealing and quenching are applied to the frame to impart shape memory properties thereto.

As shown at box 216, the device is assembled by connecting the valve construct to the frame, such that the valve construct is enclosed within a circumference of the frame. In some examples, the valve construct is connected to the frame using an adhesive, such as glue. Alternatively or in addition, suturing materials, metallic wires, and/or welding (or soldering) may be used for connecting the valve construct to the frame. As shown at box 218, following assembly, the device is delivered to the patient. The device is delivered, for example and without limitation, by a percutaneous route or by a transeptal route, each of which are known or determinable by one of ordinary skill in the art.

EXAMPLES

An Example for constructing and using the device of the present disclosure is provided. It is understood that the Example is directed to one possible embodiment of the disclosed invention and is not intended to limit the scope of the present disclosure.

Manufacturing Process:

Nitinol frame: A nitinol heart valve frame was fabricated using (1) mechanical bending, (2) a micro-laser welding, and (3) thermal shape setting and quenching processes, according to the following method. Metallic frame components were provided. The metallic frame components, such as wires and strips, were manufactured by conventional manufacturing processes, such as powder metallurgy or electroforming, as well as drawing or laser cutting processes (commercially available). Specifically, straight super-elastic Nitinol wires having a thickness of between about 0.011" to 0.018" were used for the frame. Nitinol wires were bent to make either zigzag or diamond shapes and wrapped on the aluminum mandrel. Additionally, wires were aligned parallel, then attached using the micro-laser welding process. Optimized conditions for the process were (1) 0.8-1.2 W/m2, (2) pulse, (3) beam spot size of 0.3 mm, and (4) irradiation time of 1-2 ms. The number of welded spots was 3-5 on both sides in 5 mm length. Once all structures were welded, they were thermally annealed in 500° C. for 30 to 60 min, then quenching was performed in 15° C. cool water for 5 min. The nitinol frame was dried, sterilized, and used for the heart valve fabrication.

Electrospun valve assembly: The polymer material was dissolved in solvent, such as 12% hexafluoroisopropanol (HFIP). Saline-wetted electrospun scaffolds were fabricated by a one or two stream electrospinning set up. See Hashizume, et al. The following variables for the polymer stream provided the means for forming mechanically appropriate valve structures: polymer weight percent 12%, flow rate 1.5 mL/hr, gap distance 17 cm, and voltage 11 kV. For two stream applications, a fluid, such as saline or protein, was used to enrich the fluid (e.g. cell culture medium with 10% fetal bovine serum, 2% antibiotic/antimycotic agent, 1% HEPES buffer). Stream parameters were: flow rate 1.2 mL/hr, gap distance 4.5 cm, and voltage 8 kV. The collecting mandrel was a steel cylinder of 19.1 mm diameter rotating around its major axis at 200 rpm and translating over the longitudinal direction at 0.3 cm/s. Electrospinning device metal components were autoclaved, whereas, non-metal components were sterilized with 70% ethanol and UV light.

Whole device: The PEUU electrospun leaflet were connected to the Nitinol frame structure by a combination of (1) suturing using ultra-thin nitinol or polymer thread (i.e., <100 m thick) and/or (2) by direct deposition of the PEUU electrospun layer on the Nitinol frame.

Device Delivery:

Once the valve and stent assembly were fabricated, the device was integrated into a delivery catheter system. For insertion in the catheter, the device was initially cooled to below 5° C., to allow the Nitinol material to be easily deformed (e.g., thereby converting malleable martensite phase in Nitinol). Once the device was deformed into a collapsed geometry, the device was inserted into the delivery catheter. Deployment was achieved through a pacemaker lead (or similar size of catheter) passed through the middle of the heart valve. Standard off-the-shelf delivery systems were used to deploy the device in vitro. When the device was deployed and exposed to the blood temperature (e.g., in-vitro and in-vivo animal studies), the device was conformally deployed in the tricuspid valve area.

SUMMARY

In the Example described herein, the percutaneous atrio-ventricular valve device was fabricated using a Nitinol frame and electrospun leaflets. This device was demonstrated to be collapsible to a small diameter (e.g., less than 18 F) and deployable with the pacemaker lead. Further, it was determined that the valve and stent assembly could be successfully integrated, collapsed, delivered, and deployed. This construct and delivery system has the ability to utilize conventional tissue biomaterials such as bovine pericardium, equine pericardium and porcine tissue as structural components. It is believed that the devices and methods disclosed herein represent unique approaches for tricuspid valve replacement and may be versatile for many percutaneous heart valves comprised of metallic frames that may also incorporate polymeric components.

Figure 9:
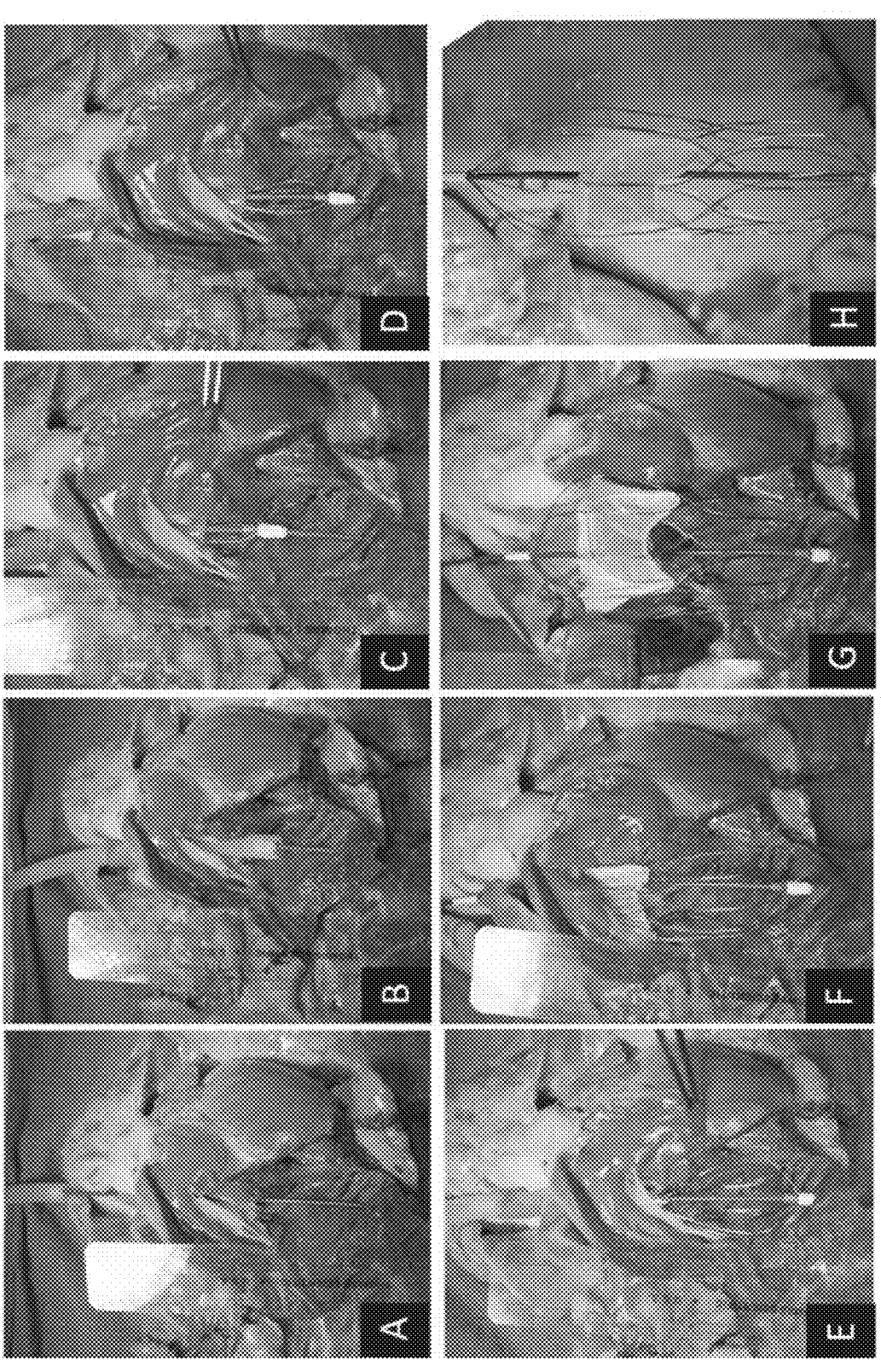
FIG. 9 is a series of photographic images showing in vivo testing of an atrioventricular prosthesis device constructed according to the principles of the present invention.

In Vivo Testing Example:

FIG. 9 is a sequence of photographic images showing an atrioventricular prosthesis device, as described herein, implanted in proximity to a cardiac valve opening. The device is inserted through a catheter and along a guidewire, as shown at A and B. As shown at C to F, the atrioventricular prosthesis device is extended from the catheter and permitted to expand from a contracted to a deployed state. The valve device is substantially fully deployed at G. An image of the device in its deployed state and removed from the cardiac tissue is shown in H.

The embodiments have been described with reference to various examples. Modifications and alterations will occur to others upon reading and understanding the foregoing examples. Accordingly, the foregoing examples are not to be construed as limiting the disclosure.

Preferred and non-limiting aspects or embodiments of the present invention will now be described in the following numbered clauses:

Clause 1. An atrioventricular prosthesis device comprising: a frame disposed on a central member extending along a longitudinal axis thereof, and at least partially defining and enclosing a central cavity, the frame having a distal portion, a proximal portion, and a middle portion connected therebetween; and a valve construct formed, at least in part, from a cell growth scaffold, at least partially disposed within the central cavity defined by the frame, the valve construct comprising: an annular portion defining an aperture and being connected to the frame for positioning the valve construct within the central cavity of the frame, and a plurality of leaflets extending longitudinally and radially inward from the annular portion, wherein the frame and the valve construct are transitionable from a contracted state, in which the frame and the valve construct are configured to be disposed within a catheter tube, and a deployed state in which a diameter of at least a portion of the frame and the valve construct substantially conforms to a diameter of a tricuspid and/or mitral valve opening.

Clause 2. The atrioventricular prosthesis device of clause 1, wherein a diameter of the middle portion of the frame is greater than a diameter of the proximal portion and a diameter of the distal portion of the frame.

Clause 3. The atrioventricular prosthesis device of clause 1 or clause 2, wherein the frame is configured to extend substantially symmetrically from at least a portion of the central member.

Clause 4. The atrioventricular prosthesis device of any of clauses 1-3, wherein the central member comprises one or more of a wire, a catheter guiderail, a catheter tube, and/or a pacemaker lead.

Clause 5. The atrioventricular prosthesis device of any of clauses 1-4, further comprising a protrusion on the distal portion of the frame, the protrusion being configured to engage a corresponding anchor disposed on the central member for advancing the frame and the valve construct along the central member.

Clause 6. The atrioventricular prosthesis device of any of clauses 1-5, wherein the proximal portion and/or the distal portion of the frame each comprise a plurality of elongated members mounted to the central member at an end of the respective portion of the frame and extending from the respective end toward the middle portion of the frame.

Clause 7. The atrioventricular prosthesis device of clause 6, wherein the distal portion of the frame comprises an annular connector slideably disposed about the central member, and wherein ends of the plurality of elongated members of the distal portion are mounted to the annular connector.

Clause 8. The atrioventricular prosthesis device of clause 6 or clause 7, wherein the plurality of elongated members each comprise a first end mounted to the central member and a second end, the second end being connected to a second end of an adjacent elongated member, thereby forming an enclosed lattice.

Clause 9. The atrioventricular prosthesis device of clause 8, wherein a portion of at least one of the enclosed lattices of the proximal portion of the frame is connected to a corresponding portion of one of the enclosed lattices of the distal portion of the frame to form an enclosed structure.

Clause 10. The atrioventricular prosthesis device of any of clauses 6-9, wherein the plurality of elongated members comprise a super-elastic, temperature-sensitive shape memory material.

Clause 11. The device of any one of clauses 6-10, wherein the plurality of elongated members are connected to other elongated members and/or to the central member by a micro-laser welding technique.

Clause 12. The atrioventricular prosthesis device of any of clauses 1-11, wherein the annular portion and/or leaflet of the valve construct comprise a polymer component formed from a biodegradable and biocompatible material, the material being selected from a group consisting of one or more of poly(ester urethane) urea (PEUU), poly(ether ester urethane)urea (PEEUU), poly(ester carbonate)urethane urea (PECUU), poly(carbonate)urethane urea (PCUU), a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(l-lactide-co-dl-lactide), a polymer comprising a lactone monomer, a polycaprolactone, polymer comprising carbonate linkages, a polycarbonate, a polyglyconate, a poly(trimethylene carbonate), a poly(glycolide-co-trimethylene carbonate), a poly(glycolide-co-trimethylene carbonate-co-dioxanone), a polyurethane, a polycarbonate urethane, a polyester urethane, a polymer comprising ester linkages, a polyalkanoate, a polyhydroxybutyrate, a polyhydroxyvalerate, a polydioxanone, a polygalactin, a natural polymer, chitosan, collagen, elastin, alginate, cellulose, hyaluronic acid and gelatin.

Clause 13. The atrioventricular prosthesis device of clause 12, wherein the polymer component is formed by electrospinning.

Clause 14. The atrioventricular prosthesis device of clause 12 or clause 13, wherein the polymer component formed by electrospinning comprises a non-woven, porous mesh material.

Clause 15. The atrioventricular prosthesis device of any of clauses 12-14, wherein the polymer component comprises a material having a porosity of at least about 60% and an average pore size of between 0.1 and 300 microns.

Clause 16. The atrioventricular prosthesis device of any of clauses 12-15, wherein the polymer component is formed by co-electrospinning a polymer suspension comprising a synthetic polymeric material and depositing an extracellular matrix gel by electrospraying.

Clause 17. The atrioventricular prosthesis device of clause 16, wherein the extracellular matrix gel is prepared by digesting decellularized tissue with an acid protease in an acidic solution to produce a digest solution, and neutralizing the digest solution to a pH ranging from 7.2 to 7.8, optionally to a pH of 7.4.

Clause 18. The atrioventricular prosthesis device of clause 16 or clause 17, wherein the extracellular matrix gel comprises at least a hydrogel portion and a liquid portion.

Clause 19. The atrioventricular prosthesis device of any of clauses 16-18, wherein a ratio of the synthetic polymer material and the extracellular matrix gel is greater than 50% polymer and less than 50% extracellular matrix gel.

Clause 20. The atrioventricular prosthesis device of clause 19, wherein the ratio is between 70% to 85% polymer material and 15% to 30% of the extracellular matrix.

Clause 21. The atrioventricular prosthesis device of any of clauses 16-20, wherein a blood component and/or a buffer solution are deposited along with the extracellular matrix material by electrospraying.

Clause 22. The atrioventricular prosthesis device of any of clauses 16-21, wherein the extracellular matrix gel is derived from mammalian tissue material, the material comprising one or more of bovine tissue, porcine tissue, equine pericardium, or a valve leaflet material.

Clause 23. The atrioventricular prosthesis device of any of clauses 1-22, wherein the frame and/or the valve construct comprise a therapeutic agent configured to be released therefrom when the device is implanted in a patient's body.

Clause 24. The atrioventricular prosthesis device of clause 23, wherein the therapeutic agent comprises one or more of a growth factor, a neurotrophic agent, an angiogenic factor, an antimicrobial agent, an anti-inflammatory agent, and/or a topical steroid.

Clause 25. The atrioventricular prosthesis device of any of clauses 1-24, wherein each of the plurality of leaflets comprises a proximal portion extending radially and longitudinally from the annular portion, a distal tip portion, and a central region extending therebetween.

Clause 26. The atrioventricular prosthesis device of clause 25, wherein edges extending about a portion of a periphery of the central region of each leaflet are partially connected to the edges of an adjacent leaflet to form commissure regions between adjacent leaflets.

Clause 27. The atrioventricular prosthesis device of clause 26, wherein each of the plurality of leaflets comprises electrospun fibers that are deposited predominantly in a circumferential direction in the central region of the leaflet, and in an axial direction in the commissure region of the leaflet.

Clause 28. The atrioventricular prosthesis device of clause 27 wherein at least 60%, and preferably 70%, of the eletrospun fibers are deposited in the circumferential direction in the central region of the leaflet.

Clause 29. The atrioventricular prosthesis device of any of clauses 26-28, wherein the central region of at least one of the plurality of leaflets defines a concave surface.

Clause 30. The atrioventricular prosthesis device of clause 29, wherein the concave surface is concave longitudinally toward the longitudinal axis of the frame and radially from edges of the leaflet toward the central region thereof.

Clause 31. The atrioventricular prosthesis device of any of clauses 26-30, wherein the central region and/or the commissure region are formed from a matrix of polymer fibers comprising an anisotropic portion with an orientation index ranging from 0.5 to 0.8.

Clause 32. The atrioventricular prosthesis device of clause 30 or clause 31, wherein the matrix at the commissure region is anisotropic with fibers of the matrix being biased in a longitudinal direction.

Clause 33. The atrioventricular prosthesis device of any of clauses 1-32, wherein the plurality of leaflets have a bending modulus ranging from 500 kPA to 500000 kPa, a mechanical strain ranging from 0 to 100, and/or a stress ranging from 0 to 5000 kPa.

Clause 34. The atrioventricular prosthesis device of any of clauses 1-33, wherein the valve construct comprises at least three leaflets extending from the annular portion thereof, thereby forming a tricuspid valve.

Clause 35. The atrioventricular prosthesis device of any of clauses 1-34, wherein the valve construct has a thickness of between 40 and 300 microns.

Clause 36. The atrioventricular prosthesis device of any of clauses 1-35 wherein the valve construct is attached to the frame by one or more of: stitching, suturing, encapsulation with membrane materials, mechanical clamps, and/or direct deposition of electrospun materials.

Clause 37. A catheter comprising a catheter tube and the atrioventricular prosthesis device of any of clauses 1-36, wherein the central member extends through at least a portion of the catheter tube and wherein the device is disposed within the catheter tube in its compressed state.

Clause 38. A method of implanting an atrioventricular valve prosthesis in a patient in need thereof, the method comprising: positioning the device of any one of clauses 1-36 to a position adjacent to an atrioventricular valve of the patient; expanding the frame and the valve construct of the device to a deployed state so that the annular portion of the valve construct is aligned with an annulus of the atrioventricular valve of the patient; and anchoring the central member extending through the device by implanting a distal end of the central member into an interior wall of a ventricle of the patient.

Clause 39. The method of clause 38, wherein positioning the device comprises positioning the device by a percutaneous route or by a transseptal route.

Clause 40. The method of clause 38 or clause 39, wherein the valve construct comprises the at least three leaflets, and wherein the atrioventricular valve is the tricuspid valve.

Clause 41. The method of clause 38 or clause 39, wherein the valve construct comprises at least two leaflets, and wherein the atrioventricular valve is a mitral valve.

The invention claimed is:

1. An atrioventricular prosthesis device comprising:
a frame comprising a plurality of flexible elongated members, the frame being configured to transition from a contracted position, where the frame is configured to be disposed within a catheter tube, to a deployed position, where the frame defines a central cavity having a width which substantially conforms to a diameter of a tricuspid and/or mitral valve opening; and
a valve construct mounted to the frame and spanning at least a portion of the central cavity defined by the frame, the valve construct comprising:
an annular portion defining an aperture connected to at least one of the plurality of elongated members, and a plurality of leaflets each comprising a central region and a commissure region, the leaflets extending longitudinally and radially inwardly from the annular portion, wherein one or more of the plurality of leaflets of the valve construct comprise a plurality of synthetic, electrospun polymer fibers deposited in an anisotropic orientation forming a non-woven, porous mesh, and wherein the central region and/or the commissure region of the plurality of leaflets comprise a matrix formed from the plurality of synthetic polymer fibers.

2. The atrioventricular prosthesis device of claim 1, wherein the frame comprises at least one collar configured to be slidably mounted to an elongated central wire or tube, and wherein the plurality of flexible elongated members are connected to the at least one collar and extend longitudinally and radially outwardly from the at least one collar to define the central cavity when the frame is in the deployed position.

3. The atrioventricular prosthesis device of claim 1, wherein the plurality of synthetic polymer fibers comprise one or more of poly(ester urethane) urea (PEUU), poly(ether ester urethane) urea (PEEUU), or poly(ester carbonate) urethane urea (PECUU), poly(carbonate) urethane urea (PCUU).

4. The atrioventricular prosthesis device of claim 1, wherein the plurality of synthetic polymer fibers comprise a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(l-lactide-co-dl-lactide).

5. The atrioventricular prosthesis device of claim 1, wherein the plurality of synthetic polymer fibers comprise at least one of: a polymer comprising a lactone monomer, a polycaprolactone, a polymer comprising carbonate linkages, a polycarbonate, a polyglyconate, a poly(trimethylene carbonate), a poly(glycolide-co-trimethylene carbonate), a poly(glycolide-co-trimethylene carbonate-co-dioxanone), a polymer comprising ester linkages, a polyalkanoate, a polyhydroxybutyrate, a polyhydroxyvalerate, a polydioxanone, or a polygalactin.

6. The atrioventricular prosthesis device of claim 1, wherein the plurality of electrospun synthetic polymer fibers form a material having a porosity of at least about 60% and an average pore size of from about 0.1 μm to about 300 μm.

7. The atrioventricular prosthesis device of claim 1, wherein the plurality of synthetic polymer fibers are anisotropic with an orientation index of from 0.5 to 0.8.

8. The atrioventricular prosthesis device of claim 1, wherein the annular portion and/or one or more of the plurality of leaflets of the valve construct further comprise an extracellular matrix gel deposited over the plurality of synthetic polymer fibers.

9. The atrioventricular prosthesis device of claim 8, wherein the extracellular matrix gel comprises decellularized tissue prepared from tissue of at least one of a human, monkey, pig, cow, or sheep.

10. The atrioventricular prosthesis device of claim 8, further comprising a blood component and/or a buffer solution deposited by electrospraying on the valve construct along with the extracellular matrix gel.

11. The atrioventricular prosthesis device of claim 8, wherein the annular portion and/or one or more of the plurality of leaflets of the valve construct comprise the plurality of synthetic polymer fibers, and wherein a ratio of synthetic polymer material and the extracellular matrix gel of the valve construct is greater than 50% synthetic polymer material and less than 50% extracellular matrix gel.

12. The atrioventricular prosthesis device of claim 8, wherein the annular portion and/or one or more of the plurality of leaflets of the valve construct comprise the plurality of synthetic polymer fibers, and wherein a ratio of synthetic polymer material and the extracellular matrix gel of the valve construct is about 70% to about 85% synthetic polymer material and about 15% to about 30% extracellular matrix gel.

13. The atrioventricular prosthesis device of claim 8, wherein the valve construct comprises extracellular matrix gel prepared by digesting decellularized tissue with an acid protease in an acidic solution to produce a digest solution, and neutralizing the digest solution to a pH ranging from 7.2 to 7.8.

14. The atrioventricular prosthesis device of claim 1, wherein the annular portion and/or one or more of the plurality of leaflets of the valve construct further comprise collagen in an amount of about 25 wt % to about 75 wt % of a total weight of the valve construct.

15. The atrioventricular prosthesis device of claim 1, wherein the frame and/or the valve construct comprise a therapeutic agent configured to be released therefrom when the device is implanted in a patient's body.

16. The atrioventricular prosthesis of claim 1, wherein the annular portion of the valve construct comprises a plurality of synthetic, electrospun polymer fibers deposited in an isotropic or anisotropic orientation forming mesh.

17. A method of manufacture of the atrioventricular prosthesis device of claim 1, the method comprising:
electrospinning a synthetic polymer material to a mandrel to form the plurality of synthetic polymer fibers of the annular portion and/or the plurality of leaflets of the valve construct;
electrospraying an extracellular matrix gel to the mandrel concurrent with electrospinning the synthetic polymer material;
connecting the plurality of flexible elongated members together to form the frame; and
mounting the valve construct to the frame, thereby forming the atrioventricular prosthesis device.

18. A method of implanting an atrioventricular valve prosthesis in a patient in need thereof, the method comprising:
positioning the atrioventricular prosthesis device of claim 1 to a position adjacent to an atrioventricular valve of the patient;
expanding the frame and valve construct of the atrioventricular prosthesis device to the deployed position so that the annular portion of the valve construct is aligned with an annulus of the atrioventricular valve of the patient; and
anchoring the atrioventricular prosthesis device to the position adjacent to the atrioventricular valve by implanting a portion of the frame into an interior wall of a ventricle of the patient.

19. The method of claim 18, wherein the valve construct comprises three leaflets and the atrioventricular valve is a tricuspid valve.

20. The method of claim 18, wherein the valve construct comprises two leaflets and the atrioventricular valve is a mitral valve.

* * * * *